US 9,187,440 B2

(12) United States Patent
Griffioen et al.

(10) Patent No.: US 9,187,440 B2
(45) Date of Patent: Nov. 17, 2015

(54) PIPERAZINE THIAZOLE DERIVATIVES USEFUL IN THE TREATMENT OF TAUOPATHIES SUCH AS ALZHEIMER'S DISEASE

(75) Inventors: Gerard Griffioen, Linden (BE); Giuseppe Cecere, Basel (CH); Matthias Nettekoven, Grenzach-Wyhlen (DE); Katrien Princen, Heverlee (BE); Hasane Ratni, Habsheim (FR); Mark Rogers-Evans, Bottmingen (CH); Walter Vifian, Gelterkinden (CH)

(73) Assignee: REMYND NV, Leuven (BE)

( * ) Notice: Subject to any disclaimer, the term of this patent is extended or adjusted under 35 U.S.C. 154(b) by 0 days.

(21) Appl. No.: 14/238,905

(22) PCT Filed: Aug. 17, 2012

(86) PCT No.: PCT/EP2012/066136
§ 371 (c)(1),
(2), (4) Date: Feb. 14, 2014

(87) PCT Pub. No.: WO2013/024168
PCT Pub. Date: Feb. 21, 2013

(65) Prior Publication Data
US 2014/0206699 A1 Jul. 24, 2014

(30) Foreign Application Priority Data

Aug. 17, 2011 (EP) ..................................... 11177742

(51) Int. Cl.
| | |
|---|---|
| *A61K 31/496* | (2006.01) |
| *C07D 285/08* | (2006.01) |
| *C07D 417/04* | (2006.01) |
| *C07D 417/12* | (2006.01) |
| *C07D 417/14* | (2006.01) |

(52) U.S. Cl.
CPC ............ *C07D 285/08* (2013.01); *C07D 417/04* (2013.01); *C07D 417/12* (2013.01); *C07D 417/14* (2013.01)

(58) Field of Classification Search
None
See application file for complete search history.

(56) References Cited

U.S. PATENT DOCUMENTS 9,023,852 B2 * 5/2015 Griffioen et al. ......... 514/252.11

FOREIGN PATENT DOCUMENTS

| WO | 2006072436 A1 | 7/2006 |
|---|---|---|
| WO | 2007090617 A2 | 8/2007 |
| WO | 2008099210 A2 | 8/2008 |
| WO | 2013/004642 * | 1/2013 |

OTHER PUBLICATIONS

Hong-Qi et al. Translational Neurodegenration, pp. 1-12 (2012).*
Ludolph et al. Eur. J.Neurol. 16(3) pp. 297-309 (2009).*
Rittman et al. ACHR, vol. 11(6),pp. 8-10 (2012).*
Yoshiyama et al. J.Neurol. Neurosurg. Psychiatry, vol. 84, p. 784-795 (2013).*
Beharry et al. Neurosci. Bull. vol. 30, pp. 346-358 (2014).*
International Prelimary Report on Patentability for PCT/EP2012/066136 dated Feb. 18, 2014. 6 pages.

* cited by examiner

*Primary Examiner* — Emily Bernhardt
(74) *Attorney, Agent, or Firm* — Lathrop & Gage LLP; James H. Velema, Esq.

(57) ABSTRACT

The present invention relates to a compound of formula (IA), wherein $G^1$ is lower alkyl; lower alkyl substituted by one or more halogens; cycloalkyl; tetrahydropyran-4-yl; phenethyl; phenethyl substituted by one or more halogens; phenoxymethyl; phenoxymethyl substituted by one or more halogens; benzyloxyethyl; benzyloxy-ethyl substituted by one or more halogens; or is —$NR^2R^3$; $R^2$ is hydrogen or lower alkyl; $R^3$ is lower alkyl; tetrahydropyran-4-yl; —$CH_2$-cycloalkyl; or cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens; X is —$CH_2$— or —$(CH_2)_2$—; Ar is phenyl or pyridinyl; $R^4$ is halogen; lower alkyl; lower alkyl substituted by one or more halogens; or lower alkoxy; n is 1 or 2; or to a pharmaceutically active salt thereof, to a stereoisomeric form, including an individual diastereoisomer or enantiomer of the compound of formula (IA) as well as to a racemic or non-racemic mixture thereof. The present invention also relates to the use of a compound of formula (IA) for treating certain neurodegenerative disorders characterized by cytotoxic TAU misfolding and/or aggregation.

(IA)

15 Claims, No Drawings

PIPERAZINE THIAZOLE DERIVATIVES USEFUL IN THE TREATMENT OF TAUOPATHIES SUCH AS ALZHEIMER'S DISEASE

RELATED APPLICATIONS

This application is a 35 U.S.C. §371 filing of International Application No. PCT/EP2012/066136, filed Aug. 17, 2012; which claims priority to European Patent Application No. 11177742.1, filed on Aug. 17, 2011. The entire contents of each are incorporated herein by reference.

FIELD OF THE INVENTION

The present invention relates to piperazine thiazoles and their use for treating certain neurodegenerative disorders characterized by cytotoxic TAU misfolding and/or aggregation.

BACKGROUND OF THE INVENTION

TAU is a protein with the ability to bind—and consequently stabilise and define—microtubule structure and function in neurons. The binding of TAU to microtubules is regulated by phosphorylation of TAU and several TAU phosphorylation sites and their corresponding kinases have been identified which control phosphorylation status of TAU and consequently modulate the affinity of TAU-binding to microtubules.

Hyperphosphorylation of TAU cause it to aggregate in an insoluble form. (These aggregations of hyperphosphorylated TAU protein are also referred to as PHF, or "paired helical filaments"). Tauopathies are characterised by insoluble aggregates or polymers of hyperphosphorylated TAU which are formed by self-polymerisation of TAU monomers.

An important aspect of the TAU aggregation is its associated cytotoxicity which reduces neuronal integrity and functionality and ultimately resulting in disease symptoms. A direct role of TAU in disease onset has been established unequivocally by the elucidation of familial mutations in TAU which appear to be responsible for a very early and sometimes aggressive form of tauopathy. Such mutations comprise changes in the amino acid sequence of TAU that—directly or indirectly—promote neurotoxic aggregation.

Alzheimer's disease is the best known of these, where TAU protein is deposited within neurons in the form of neurofibrillary tangles (NFTs). They were first described by the eponymous Alois Alzheimer in one of his patients suffering from the disorder.

Currently used treatments for tauopathies, including Alzheimer's disease, offer only symptomatic benefit without impacting the underlying neurodegeneration.

WO2007/090617 discloses substituted 1,2,4-thiadiazole derivatives for use in the treatment of an α-synucleopathy such as Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease.

Treatments aimed to suppress cytotoxic TAU misfolding and/or aggregation in order to delay or halt the progression of disease are presently not available. Thus there is a need for new treatments that target the underlying molecular mechanism of noxious TAU misfolding and/or aggregation in order to reduce neuronal cell death and/or degeneration in patients suffering from tauopathies such as Alzheimer's disease.

SUMMARY OF THE INVENTION

A first aspect of the present invention relates to compounds of formula IA or to a pharmaceutically active salt thereof, to a stereoisomeric form, including an individual diastereoisomer or enantiomer of the compound of formula IA as well as to a racemic or non-racemic mixture thereof;

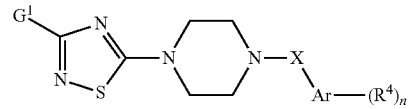

IA wherein $G^1$ is lower alkyl; lower alkyl substituted by one or more halogens; cycloalkyl; tetrahydropyran-4-yl; phenethyl; phenethyl substituted by one or more halogens; phenoxymethyl; phenoxymethyl substituted by one or more halogens; benzyloxy-ethyl; benzyloxy-ethyl substituted by one or more halogens; or is $-NR^2R^3$;

$R^2$ is hydrogen or lower alkyl;

$R^3$ is lower alkyl; tetrahydropyran-4-yl; $-CH_2$-cycloalkyl; or cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens;

X is $-CH_2-$ or $-(CH_2)_2-$;

Ar is phenyl or pyridinyl;

$R^4$ is halogen; lower alkyl; lower alkyl substituted by one or more halogens; or lower alkoxy;

n is 1 or 2;

with the proviso that said compound is not:
  5-(4-(3-fluorobenzyl)piperazin-1-yl)-3-methyl-1,2,4-thiadiazole and
  3-isopropyl-5-(4-(3-(trifluoromethyl)benzyl)piperazin-1-yl)-1,2,4-thiadiazole.

A second aspect of the invention relates to a process for preparation of compounds of formula IA according to a first aspect of the invention, which process comprises coupling a compound of formula

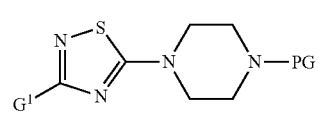

IV with a compound of formula

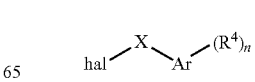

to give a compound of formula

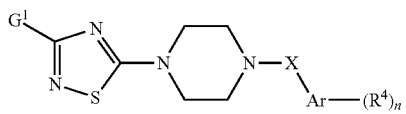

IA wherein the definitions are as described in the first aspect of the invention, wherein PG is hydrogen or a protecting group, such as tert-butyloxycarbonyl (BOC), 9-fluorenylmethyloxycarbonyl (FMOC) and the like, and hal is a halogen or if desired, converting the compounds obtained into pharmaceutically acceptable acid addition salts.

A third aspect of the invention relates to a medicament containing one or more compounds according to the first aspect of the invention and pharmaceutically acceptable excipients.

A fourth aspect of the invention relates to a medicament according to the third aspect, for use in the treatment of a disease selected from the group consisting of are Alzheimer's disease, Pick's disease, corticobasal degeneration, progressive supranuclear palsy, frontotemporal dementia, and parkinsonism (linked to chromosome 17, FTDP-17).

A fifth aspect of the invention relates to the use of a compound according to the first aspect of the invention for the manufacture of medicaments for the treatment of Alzheimer's disease, Pick's disease, corticobasal degeneration, progressive supranuclear palsy, frontotemporal dementia and parkinsonism (linked to chromosome 17, FTDP-17).

A sixth aspect of the invention relates to a method for the treatment of Alzheimer's disease, Pick's disease, corticobasal degeneration, progressive supranuclear palsy, frontotemporal dementia and parkinsonism (linked to chromosome 17, FTDP-17), which method comprising administering an effective amount of a compound as defined in the first aspect of the invention.

DETAILED DESCRIPTION

In an embodiment, the present invention encompasses a compound of formula IA, wherein, $G^1$ is lower alkyl; lower alkyl substituted by one or more halogens; cycloalkyl; tetrahydropyran-4-yl; phenethyl; phenethyl substituted by one or more halogens; phenoxymethyl; phenoxymethyl substituted by one or more halogens; benzyloxy-ethyl; benzyloxy-ethyl substituted by one or more halogens; or is —$NR^2R^3$; preferably, $G^1$ is $C_{1-7}$alkyl; $C_{1-7}$alkyl substituted by one or more halogens; $C_{3-6}$cycloalkyl; tetrahydropyran-4-yl; phenethyl; phenethyl substituted by one or more halogens; phenoxymethyl; phenoxymethyl substituted by one or more halogens; benzyloxy-ethyl; benzyloxy-ethyl substituted by one or more halogens; or is —$NR^2R^3$; preferably $G^1$ is lower alkyl; cycloalkyl; tetrahydropyran-4-yl; phenoxymethyl substituted by one or more halogens; benzyloxy-ethyl; benzyloxy-ethyl substituted by one or more halogens; or is —$NR^2R^3$; preferably, $G^1$ is lower alkyl; cycloalkyl; phenoxymethyl substituted by one or more halogens; benzyloxy-ethyl; benzyloxy-ethyl substituted by one or more halogens; or is —$NR^2R^3$; preferably, $G^1$ is lower alkyl; phenoxymethyl substituted by one or more halogens; benzyloxy-ethyl substituted by halogen; or is —$NR^2R^3$; preferably, $G^1$ is $C_{1-7}$alkyl; phenoxymethyl substituted by one or more halogens; benzyloxy-ethyl substituted by one or more halogens; or is —$NR^2R^3$;

$R^2$ is hydrogen or lower alkyl; preferably $R^2$ is hydrogen or $C_{1-7}$alkyl $R^3$ is lower alkyl; tetrahydropyran-4-yl; —$CH_2$-cycloalkyl; cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens; preferably, $R^3$ is $C_{1-7}$alkyl; tetrahydropyran-4-yl; —$CH_2$—$C_{3-6}$ cycloalkyl; $C_{3-6}$cycloalkyl optionally substituted by $C_{1-7}$alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or $C_{1-7}$alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or $C_{1-7}$alkyl substituted by one or more halogens; preferably, $R^3$ is tetrahydropyran-4-yl; —$CH_2$-cycloalkyl; cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens; preferably, $R^3$ is cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens;

X is —$CH_2$— or —$(CH_2)_2$—; preferably X is —$(CH_2)_2$;

Ar is phenyl or pyridinyl; preferably Ar is phenyl;

$R^4$ is halogen; lower alkyl; lower alkyl substituted by one or more halogens; or lower alkoxy; preferably $R^4$ is halogen; $C_{1-7}$alkyl; $C_{1-7}$alkyl substituted by one or more halogens; or $C_{1-7}$alkoxy; preferably $R^4$ is halogen; lower alkyl substituted by one or more halogens; or lower alkoxy; preferably $R^4$ is halogen; or lower alkoxy;

n is 1 or 2; preferably, n is 1.

In an embodiment, the present invention provides compounds of formula IA, wherein, $G^1$ is $C_{1-6}$alkyl; $C_{1-6}$alkyl substituted by one or more halogens; $C_{3-6}$cycloalkyl; tetrahydropyran-4-yl; phenethyl; phenethyl substituted by one or more halogens; phenoxymethyl; phenoxymethyl substituted by one or more halogens; benzyloxy-ethyl; benzyloxy-ethyl substituted by one or more halogens; or is —$NR^2R^3$; preferably, $G^1$ is $C_{1-6}$alkyl; $C_{3-6}$cycloalkyl; tetrahydropyran-4-yl; phenoxymethyl substituted by one or more halogens; benzyloxy-ethyl; benzyloxy-ethyl substituted by one or more halogens; or is —$NR^2R^3$; preferably, $G^1$ is $C_{1-6}$alkyl; $C_{3-6}$cycloalkyl; phenoxymethyl substituted by one or more halogens; benzyloxy-ethyl; benzyloxy-ethyl substituted by one or more halogens; or is —$NR^2R^3$; preferably, $G^1$ is $C_{1-6}$alkyl; phenoxymethyl substituted by one or more halogens; benzyloxy-ethyl; benzyloxy-ethyl substituted by one or more halogens; or is —$NR^2R^3$;

$R^2$ is hydrogen or $C_{1-6}$alkyl;

$R^3$ is $C_{1-6}$alkyl; tetrahydropyran-4-yl; —$CH_2$—$C_{3-6}$cycloalkyl; $C_{3-6}$cycloalkyl optionally substituted by $C_{1-6}$alkyl substituted by one or more halogens; or $R^2$ and R³ form together with the N-atom to which they are attached a heterocycloalkyl group with 4 or 5 carbon atoms, which is optionally substituted by one or more substituents selected from halogen; or $C_{1-6}$alkyl substituted by one or more halogens; preferably, R³ is tetrahydropyran-4-yl; —CH₂—$C_{3-6}$cycloalkyl; $C_{3-6}$cycloalkyl optionally substituted by $C_{1-6}$alkyl substituted by one or more halogens; or R² and R³ form together with the N-atom to which they are attached a heterocycloalkyl group with 4 or 5 carbon atoms, which is optionally substituted by one or more substituents selected from halogen; or $C_{1-6}$alkyl substituted by one or more halogens; preferably, R³ is $C_{3-6}$cycloalkyl optionally substituted by $C_{1-6}$alkyl substituted by one or more halogens; or R² and R³ form together with the N-atom to which they are attached a heterocycloalkyl group with 4 or 5 carbon atoms, which is optionally substituted by one or more substituents selected from halogen; or $C_{1-6}$alkyl substituted by one or more halogens;

X is —CH₂— or —(CH₂)₂—; preferably X is —(CH₂)₂;

Ar is phenyl or pyridinyl; preferably Ar is phenyl;

R⁴ is halogen; $C_{1-6}$alkyl; $C_{1-6}$alkyl substituted by one or more halogens; or $C_{1-6}$alkoxy; preferably R⁴ is halogen; $C_{1-6}$alkyl substituted by one or more halogens; or $C_{1-6}$alkoxy; preferably R⁴ is halogen; or $C_{1-6}$alkoxy;

n is 1 or 2; preferably, n is 1.

In an embodiment, the present invention encompasses a compound of formula IA, wherein, G¹ is selected from: lower alkyl; cycloalkyl; tetrahydropyran-4-yl; phenoxymethyl substituted by one or more halogens; benzyloxy-ethyl; benzyloxy-ethyl substituted by one or more halogens; or —NR²R³.

In another particular embodiment of the present invention, the compounds have a structure according to formula IA, wherein G¹ is —NR²R³ and R³ is cycloalkyl optionally substituted by lower alkyl substituted by one or more halogens; or R² and R³ form together with the N-atom to which they are attached a heterocycloalkyl group with 4 or 5 carbon atoms, which is optionally substituted by one or more substituents selected from halogen; or lower alkyl substituted by one or more halogens.

In an embodiment, the present invention encompasses a compound of formula IA, wherein, G¹ is selected from: lower alkyl; cycloalkyl; tetrahydropyran-4-yl; phenoxymethyl substituted by one or more halogens; benzyloxy-ethyl; benzyloxy-ethyl substituted by one or more halogens; or —NR²R³; and X is —(CH₂)₂; yet more in particular G¹ is lower alkyl or phenoxymethyl substituted by one or more halogens; yet more in particular G¹ is benzyloxy-ethyl; or phenoxymethyl substituted by one or more halogens; yet more in particular G¹ is phenoxymethyl substituted by one or more halogens.

In an embodiment, the present invention encompasses a compound of formula IA, wherein, X is —(CH₂)₂.

In an embodiment, the present invention encompasses a compound of formula IA, wherein Ar is phenyl.

In an embodiment, the present invention encompasses a compound of formula IA, wherein, G¹ is selected from: lower alkyl; cycloalkyl; tetrahydropyran-4-yl; phenoxymethyl substituted by one or more halogens; benzyloxy-ethyl; benzyloxy-ethyl substituted by one or more halogens; or —NR²R³; and Ar is phenyl; yet more in particular G¹ is lower alkyl or benzyloxy-ethyl; phenoxymethyl substituted by one or more halogens; yet more in particular G¹ is phenoxymethyl substituted by one or more halogens.

In an embodiment, the present invention encompasses a compound of formula IA, wherein, G¹ is selected from: lower alkyl; cycloalkyl; tetrahydropyran-4-yl; phenoxymethyl substituted by one or more halogens; benzyloxy-ethyl; benzyloxy-ethyl substituted by one or more halogens; or —NR²R³; and Ar is phenyl; yet more in particular G¹ is lower alkyl or phenoxymethyl substituted by one or more halogens; yet more in particular G¹ is lower alkyl.

In an embodiment, the present invention encompasses a compound of formula IA, wherein, G¹ is selected from: lower alkyl; cycloalkyl; tetrahydropyran-4-yl; phenoxymethyl substituted by one or more halogens; benzyloxy-ethyl; or benzyloxy-ethyl substituted by one or more halogens.

In another particular embodiment of the present invention, the compounds have a structure according to formula IA, whereby G¹ is —NR²R³.

In another particular embodiment of the present invention, the compounds have a structure according to formula IA, whereby G¹ is —NR²R³; R² is hydrogen; and R³ is lower alkyl; tetrahydropyran-4-yl; —CH₂-cycloalkyl; or cycloalkyl optionally substituted by lower alkyl substituted by one or more halogens.

In another particular embodiment of the present invention, the compounds have a structure according to formula IA, whereby G¹ is —NR²R³; and R² and R³ form together with the N-atom to which they are attached a heterocycloalkyl group with 4 or 5 carbon atoms, which is optionally substituted by one or more substituents selected from halogen; or lower alkyl substituted by one or more halogens.

In another particular embodiment of the present invention, the compounds have a structure according to formula IA, wherein G¹ is benzyloxy-ethyl optionally substituted by one or more halogens and Ar is phenyl.

In another particular embodiment of the present invention, the compounds have a structure according to formula IA, wherein G¹ is benzyloxy-ethyl; Ar is phenyl and X is —(CH₂)₂.

In another particular embodiment of the present invention, the compounds have a structure according to formula IA, wherein G¹ is phenoxymethyl substituted by one or more halogens and Ar is phenyl.

In another particular embodiment of the present invention, the compounds have a structure according to formula IA, wherein G¹ is phenoxymethyl substituted by one or more halogens; Ar is phenyl and X is —(CH₂)₂.

In another particular embodiment of the present invention, the compounds have a structure according to formula IA, wherein G¹ is lower alkyl and Ar is phenyl.

In another particular embodiment of the present invention, the compounds have a structure according to formula IA, wherein G¹ is lower alkyl; Ar is phenyl and X is —(CH₂)₂.

In a particular embodiment of the invention, the compounds have a structure of formula IA, whereby G¹ is —NR²R³; and Ar is phenyl.

In a particular embodiment of the invention, the compounds have a structure of formula IA, whereby G¹ is —NR²R³; Ar is phenyl and R² and R³ form together with the N-atom to which they are attached a heterocycloalkyl group with 4 or 5 carbon atoms, which is optionally substituted by one or more substituents selected from halogen; or lower alkyl substituted by one or more halogens.

In a particular embodiment of the invention, the compounds have a structure of formula IA, whereby G¹ is —NR²R³; X is —(CH₂)₂— and R² and R³ form together with the N-atom to which they are attached a heterocycloalkyl group with 4 or 5 carbon atoms, which is optionally substituted by one or more substituents selected from halogen; or lower alkyl substituted by one or more halogens.

In a particular embodiment of the invention, the compounds have a structure of formula IA, whereby G¹ is —NR²R³; Ar is phenyl; R² and R³ form together with the N-atom to which they are attached a heterocycloalkyl group with 4 or 5 carbon atoms, which is optionally substituted by one or more substituents selected from halogen; or lower alkyl substituted by one or more halogens; and X is —(CH$_2$)$_2$.

For example, the present invention encompasses compounds of formula IA having structural formula I,

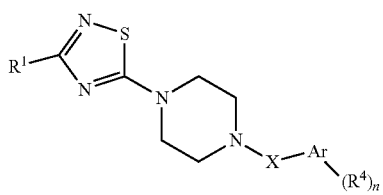

wherein R$^1$ has the same meaning as G$^1$.

In a particular embodiment, the present invention relates to the following compounds, uses, medicaments and processes:

E1. A compound of formula I

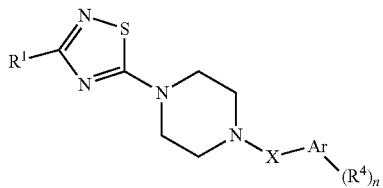

wherein
R$^1$ is lower alkyl; cycloalkyl; tetrahydropyran-4-yl or is —NR$^2$R$^3$;
R$^2$ is hydrogen or lower alkyl;
R$^3$ is lower alkyl; tetrahydropyran-4-yl; —CH$_2$-cycloalkyl or cycloalkyl optionally substituted by lower alkyl substituted by one or more halogens;
or R$^2$ and R$^3$ form together with the N-atom to which they are attached a heterocycloalkyl group with 4 or 5 carbon atoms, which is optionally substituted by one or more substituents selected from halogen or lower alkyl substituted by one or more halogens;
X is —CH$_2$— or —(CH$_2$)$_2$—;
Ar is phenyl or pyridinyl;
R$^4$ is halogen, lower alkyl or lower alkyl substituted by one or more halogens;
n is 1 or 2;
or to a pharmaceutically active salt thereof, to a stereoisomeric form, including an individual diastereoisomer or enantiomer of the compound of formula I as well as to a racemic or non-racemic mixture thereof.

E2. A compound of formula I according to E1, wherein X is —(CH$_2$)$_2$—.

E3. A compound of formula I according to E2, which compounds are:

1-[3-(4,4-Difluoro-piperidin-1-yl)-[1,2,4]thiadiazol-5-yl]-4-[2-(4-methoxy-phenyl)-ethyl]-piperazine
1-[2-(4-Chloro-phenyl)-ethyl]-4-[3-(4,4-difluoro-piperidin-1-yl)-[1,2,4]thiadiazol-5-yl]-piperazine
1-[2-(4-Chloro-phenyl)-ethyl]-4-[3-(3,3-difluoro-pyrrolidin-1-yl)-[1,2,4]thiadiazol-5-yl]-piperazine
1-[2-(4-Chloro-phenyl)-ethyl]-4-[3-(4-fluoro-piperidin-1-yl)-[1,2,4]thiadiazol-5-yl]-piperazine
1-[2-(4-Chloro-phenyl)-ethyl]-4-[3-(4-trifluoromethyl-piperidin-1-yl)-[1,2,4]thiadiazol-5-yl]-piperazine
1-[2-(4-Chloro-phenyl)-ethyl]-4-(3-piperidin-1-yl-[1,2,4]thiadiazol-5-yl)-piperazine
(5-{4-[2-(4-Chloro-phenyl)-ethyl]-piperazin-1-yl}-[1,2,4]thiadiazol-3-yl)-cyclopropylmethyl-amine
(5-{4-[2-(4-Chloro-phenyl)-ethyl]-piperazin-1-yl}-[1,2,4]thiadiazol-3-yl)-(tetrahydro-pyran-4-yl)-amine
(5-{4-[2-(4-Chloro-phenyl)-ethyl]-piperazin-1-yl}-[1,2,4]thiadiazol-3-yl)-cyclohexyl-amine
1-[2-(3,4-Difluoro-phenyl)-ethyl]-4-[3-(4,4-difluoro-piperidin-1-yl)-[1,2,4]thiadiazol-5-yl]-piperazine
1-[2-(3,4-Difluoro-phenyl)-ethyl]-4-[3-(3,3-difluoro-pyrrolidin-1-yl)-[1,2,4]thiadiazol-5-yl]-piperazine
1-[2-(3,4-Difluoro-phenyl)-ethyl]-4-[3-(4-fluoro-piperidin-1-yl)-[1,2,4]thiadiazol-5-yl]-piperazine
1-[2-(3,4-Difluoro-phenyl)-ethyl]-4-[3-(4-trifluoromethyl-piperidin-1-yl)-[1,2,4]thiadiazol-5-yl]-piperazine
1-[2-(3,4-Difluoro-phenyl)-ethyl]-4-(3-pyrrolidin-1-yl-[1,2,4]thiadiazol-5-yl)-piperazine
Cyclopropylmethyl-(5-{4-[2-(3,4-difluoro-phenyl)-ethyl]-piperazin-1-yl}-[1,2,4]thiadiazol-3-yl)-amine
(5-{4-[2-(3,4-Difluoro-phenyl)-ethyl]-piperazin-1-yl}-[1,2,4]thiadiazol-3-yl)-(tetrahydro-pyran-4-yl)-amine
Cyclohexyl-(5-{4-[2-(3,4-difluoro-phenyl)-ethyl]-piperazin-1-yl}-[1,2,4]thiadiazol-3-yl)-amine
1-[2-(3,4-Difluoro-phenyl)-ethyl]-4-(3-piperidin-1-yl-[1,2,4]thiadiazol-5-yl)-piperazine
(5-{4-[2-(3,4-Difluoro-phenyl)-ethyl]-piperazin-1-yl}-[1,2,4]thiadiazol-3-yl)-(4-trifluoromethyl-cyclohexyl)-amine
Butyl-(5-{4-[2-(3,4-difluoro-phenyl)-ethyl]-piperazin-1-yl}-[1,2,4]thiadiazol-3-yl)-ethyl-amine
1-(3-Cyclohexyl-[1,2,4]thiadiazol-5-yl)-4-[2-(4-methoxy-phenyl)-ethyl]-piperazine
1-(3-Cyclohexyl-[1,2,4]thiadiazol-5-yl)-4-[2-(3-methoxy-phenyl)-ethyl]-piperazine
1-(3-Butyl-[1,2,4]thiadiazol-5-yl)-4-[2-(4-methoxy-phenyl)-ethyl]-piperazine
1-(3-Cyclopropyl-[1,2,4]thiadiazol-5-yl)-4-[2-(4-methoxy-phenyl)-ethyl]-piperazine
1-(3-Butyl-[1,2,4]thiadiazol-5-yl)-4-[2-(3-methoxy-phenyl)-ethyl]-piperazine
1-(3-Cyclopropyl-[1,2,4]thiadiazol-5-yl)-4-[2-(3-methoxy-phenyl)-ethyl]-piperazine
1-[2-(4-Fluoro-phenyl)-ethyl]-4-[3-(tetrahydro-pyran-4-yl)-[1,2,4]thiadiazol-5-yl]-piperazine
1-[2-(4-Methoxy-phenyl)-ethyl]-4-[3-(tetrahydro-pyran-4-yl)-[1,2,4]thiadiazol-5-yl]-piperazine
1-[2-(2-Methoxy-pyridin-4-yl)-ethyl]-4-[3-(tetrahydro-pyran-4-yl)-[1,2,4]thiadiazol-5-yl]-piperazine or
1-[2-(3,4-Difluoro-phenyl)-ethyl]-4-[3-(tetrahydro-pyran-4-yl)-[1,2,4]thiadiazol-5-yl]-piperazine.

E4. A compound of formula I according to any one of E1-E3, wherein R$^1$ is lower alkyl, cycloalkyl or tetrahydropyran-4-yl.

E5. A compound of formula I according to E4, wherein the compounds are:

1-(3-Cyclohexyl-[1,2,4]thiadiazol-5-yl)-4-[2-(4-methoxy-phenyl)-ethyl]-piperazine
1-(3-Cyclohexyl-[1,2,4]thiadiazol-5-yl)-4-[2-(3-methoxy-phenyl)-ethyl]-piperazine
1-(3-Butyl-[1,2,4]thiadiazol-5-yl)-4-[2-(4-methoxy-phenyl)-ethyl]-piperazine
1-(3-Cyclopropyl-[1,2,4]thiadiazol-5-yl)-4-[2-(4-methoxy-phenyl)-ethyl]-piperazine
1-(3-Butyl-[1,2,4]thiadiazol-5-yl)-4-[2-(3-methoxy-phenyl)-ethyl]-piperazine
1-(3-Cyclopropyl-[1,2,4]thiadiazol-5-yl)-4-[2-(3-methoxy-phenyl)-ethyl]-piperazine 1-[2-(4-Fluoro-phenyl)-ethyl]-4-[3-(tetrahydro-pyran-4-yl)-[1,2,4]thiadiazol-5-yl]-piperazine 1-[2-(4-Methoxy-phenyl)-ethyl]-4-[3-(tetrahydro-pyran-4-yl)-[1,2,4]thiadiazol-5-yl]-piperazine 1-[2-(2-Methoxy-pyridin-4-yl)-ethyl]-4-[3-(tetrahydro-pyran-4-yl)-[1,2,4]thiadiazol-5-yl]-piperazine or 1-[2-(3,4-Difluoro-phenyl)-ethyl]-4-[3-(tetrahydro-pyran-4-yl)-[1,2,4]thiadiazol-5-yl]-piperazine.

E6. A compound of formula I according to any one of E1-E3, wherein $R^1$ is —$NR^2R^3$.

E7. A compound of formula I according to E6, wherein $R^2$ is hydrogen and $R^3$ is lower alkyl, tetrahydropyran-4-yl, —$CH_2$-cycloalkyl or cycloalkyl optionally substituted by lower alkyl substituted by one or more halogens.

E8. A compound of formula I according to E7, wherein the compounds are (5-{4-[2-(4-Chloro-phenyl)-ethyl]-piperazin-1-yl}-[1,2,4]thiadiazol-3-yl)-cyclopropylmethyl-amine (5-{4-[2-(4-Chloro-phenyl)-ethyl]-piperazin-1-yl}-[1,2,4]thiadiazol-3-yl)-(tetrahydro-pyran-4-yl)-amine (5-{4-[2-(4-Chloro-phenyl)-ethyl]-piperazin-1-yl}-[1,2,4]thiadiazol-3-yl)-cyclohexyl-amine Cyclopropylmethyl-(5-{4-[2-(3,4-difluoro-phenyl)-ethyl]-piperazin-1-yl}-[1,2,4]thiadiazol-3-yl)-amine (5-{4-[2-(3,4-Difluoro-phenyl)-ethyl]-piperazin-1-yl}-[1,2,4]thiadiazol-3-yl)-(tetrahydro-pyran-4-yl)-amine Cyclohexyl-(5-{4-[2-(3,4-difluoro-phenyl)-ethyl]-piperazin-1-yl}-[1,2,4]thiadiazol-3-yl)-amine or (5-{4-[2-(3,4-Difluoro-phenyl)-ethyl]-piperazin-1-yl}-[1,2,4]thiadiazol-3-yl)-(4-trifluoromethyl-cyclohexyl)-amine E9. A compound of formula I according to E6, wherein $R^2$ and $R^3$ form together with the N-atom to which they are attached a heterocycloalkyl group with 4 or 5 carbon atoms, which is optionally substituted by one or more substituents selected from halogen or lower alkyl substituted by one or more halogens.

E10. A compound of formula I according to E9, which compounds are:

1-[3-(4,4-Difluoro-piperidin-1-yl)-[1,2,4]thiadiazol-5-yl]-4-[2-(4-methoxy-phenyl)-ethyl]-piperazine 1-[2-(4-Chloro-phenyl)-ethyl]-4-[3-(4,4-difluoro-piperidin-1-yl)-[1,2,4]thiadiazol-5-yl]-piperazine 1-[2-(4-Chloro-phenyl)-ethyl]-4-[3-(3,3-difluoro-pyrrolidin-1-yl)-[1,2,4]thiadiazol-5-yl]-piperazine 1-[2-(4-Chloro-phenyl)-ethyl]-4-[3-(4-fluoro-piperidin-1-yl)-[1,2,4]thiadiazol-5-yl]-piperazine 1-[2-(4-Chloro-phenyl)-ethyl]-4-[3-(4-trifluoromethyl-piperidin-1-yl)-[1,2,4]thiadiazol-5-yl]-piperazine 1-[2-(4-Chloro-phenyl)-ethyl]-4-(3-piperidin-1-yl-[1,2,4]thiadiazol-5-yl)-piperazine 1-[2-(3,4-Difluoro-phenyl)-ethyl]-4-[3-(4,4-difluoro-piperidin-1-yl)-[1,2,4]thiadiazol-5-yl]-piperazine 1-[2-(3,4-Difluoro-phenyl)-ethyl]-4-[3-(3,3-difluoro-pyrrolidin-1-yl)-[1,2,4]thiadiazol-5-yl]-piperazine 1-[2-(3,4-Difluoro-phenyl)-ethyl]-4-[3-(4-fluoro-piperidin-1-yl)-[1,2,4]thiadiazol-5-yl]-piperazine 1-[2-(3,4-Difluoro-phenyl)-ethyl]-4-[3-(4-trifluoromethyl-piperidin-1-yl)-[1,2,4]thiadiazol-5-yl]-piperazine 1-[2-(3,4-Difluoro-phenyl)-ethyl]-4-(3-pyrrolidin-1-yl-[1,2,4]thiadiazol-5-yl)-piperazine or 1-[2-(3,4-Difluoro-phenyl)-ethyl]-4-(3-piperidin-1-yl-[1,2,4]thiadiazol-5-yl)-piperazine E11. A process for preparation of compounds of formula I according to E1, which process comprises coupling a compound of formula

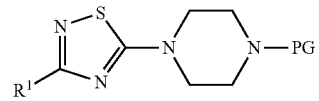

with a compound of formula

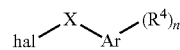

to give a compound of formula

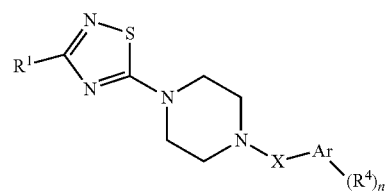

wherein the definitions are as described in E1, or if desired, converting the compounds obtained into pharmaceutically acceptable acid addition salts.

E12. A compound according to any one of E1-E10, when manufactured according to a process of E11.

E13. A compound according to any one of E1-E10 for use as therapeutically active substance.

E14. A medicament containing one or more compounds as described in any one of E1 to E10 and pharmaceutically acceptable excipients.

E15. A medicament according to E14, wherein the illnesses which may be treated are Alzheimer's disease, Pick's disease, corticobasal degeneration, progressive supranuclear palsy, frontotemporal dementia and parkinsonism (linked to chromosome 17, FTDP-17).

E16. The use of a compound as described in any one of E1-E10 for the treatment of Alzheimer's disease, Pick's disease, corticobasal degeneration, progressive supranuclear palsy, frontotemporal dementia and parkinsonism (linked to chromosome 17, FTDP-17).

E17. The use of a compound as described in any one of E1-E10 for the manufacture of medicaments for the treatment of Alzheimer's disease, Pick's disease, corticobasal degeneration, progressive supranuclear palsy, frontotemporal dementia and parkinsonism (linked to chromosome 17, FTDP-17).

E18. A method for the treatment of Alzheimer's disease, Pick's disease, corticobasal degeneration, progressive supranuclear palsy, frontotemporal dementia and parkinsonism (linked to chromosome 17, FTDP-17), which method comprising administering an effective amount of a compound as defined in any one of E1-E10.

E19. The invention as hereinbefore described.

For example, the present invention encompasses a compound or formula I or IA wherein $G^1$ has the same meaning as defined for $R^1$, wherein, $R^1$ is lower alkyl; cycloalkyl; tetrahydropyran-4-yl; or is —$NR^2R^3$; preferably, $R^1$ is $C_{1-7}$alkyl; $C_{3-6}$cycloalkyl; tetrahydropyran-4-yl; or is —$NR^2R^3$; preferably, $R^1$ is $C_{1-6}$alkyl; $C_{3-6}$cycloalkyl; tetrahydropyran-4-yl; or is —$NR^2R^3$; preferably, $R^1$ is lower alkyl; cycloalkyl; or is —$NR^2R^3$; preferably, $R^1$ is lower alkyl; or is —$NR^2R^3$;

$R^2$ is hydrogen or lower alkyl; preferably $R^2$ is hydrogen or $C_{1-7}$alkyl; preferably $R^2$ is hydrogen or $C_{1-6}$alkyl;

$R^3$ is lower alkyl; tetrahydropyran-4-yl; —$CH_2$-cycloalkyl; cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens; preferably $R^3$ is $C_{1-7}$alkyl; tetrahydropyran-4-yl; —$CH_2$—$C_{3-6}$cycloalkyl; $C_{3-6}$cycloalkyl optionally substituted by $C_{1-7}$alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or $C_{1-7}$alkyl substituted by one or more halogens; preferably $R^3$ is $C_{1-6}$alkyl; tetrahydropyran-4-yl; —$CH_2$—$C_{3-6}$cycloalkyl; $C_{3-6}$cycloalkyl optionally substituted by $C_{1-6}$alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or $C_{1-6}$alkyl substituted by one or more halogens; preferably, $R^3$ is tetrahydropyran-4-yl; —$CH_2$-cycloalkyl; cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens; preferably, $R^3$ is cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens;

X is —$CH_2$— or —$(CH_2)_2$—; preferably X is —$(CH_2)_2$;

Ar is phenyl or pyridinyl; preferably Ar is phenyl;

$R^4$ is halogen; lower alkyl; or lower alkyl substituted by one or more halogens; or lower alkoxy; preferably $R^4$ is halogen; $C_{1-7}$alkyl; or $C_{1-7}$alkyl substituted by one or more halogens; or $C_{1-7}$alkoxy; preferably $R^4$ is halogen; $C_{1-6}$alkyl; or $C_{1-6}$alkyl substituted by one or more halogens; or $C_{1-6}$alkoxy; preferably $R^4$ is halogen; lower alkyl substituted by one or more halogens; preferably $R^4$ is halogen;

n is 1 or 2; preferably, n is 1.

In a yet more particular embodiment, the present invention encompasses compounds according to formula I or IA, wherein, $R^1$ is selected from: lower alkyl; cycloalkyl; tetrahydropyran-4-yl; or —$NR^2R^3$;

In another particular embodiment of the present invention, the compounds have a structure according to formula I or IA, wherein $R^1$ is —$NR^2R^3$ and $R^3$ is cycloalkyl optionally substituted by lower alkyl substituted by one or more halogens; or $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens.

In an embodiment, the present invention encompasses a compound of formula I or IA, wherein, $R^1$ is selected from: lower alkyl; cycloalkyl; tetrahydropyran-4-yl; or —$NR^2R^3$; and X is —$(CH_2)_2$; yet more in particular $R^1$ is lower alkyl or cycloalkyl; yet more in particular $R^1$ is lower alkyl.

In an embodiment, the present invention encompasses a compound of formula I or IA, wherein, X is —$(CH_2)_2$.

In an embodiment, the present invention encompasses compounds of formula I or IA, wherein Ar is phenyl.

In an embodiment, the present invention encompasses compounds of formula I or IA, wherein, $R^1$ is selected from: lower alkyl; cycloalkyl; tetrahydropyran-4-yl; or —$NR^2R^3$; and Ar is phenyl; yet more in particular $R^1$ is lower alkyl or cycloalkyl; yet more in particular $R^1$ is lower alkyl.

In another particular embodiment of the present invention, the compounds have a structure according to formula I or IA, whereby $R^1$ is —$NR^2R^3$.

In another particular embodiment of the present invention, the compounds have a structure according to formula I or IA, whereby $R^1$ is —$NR^2R^3$; $R^2$ is hydrogen; and $R^3$ is lower alkyl; tetrahydropyran-4-yl; —$CH_2$-cycloalkyl; or cycloalkyl optionally substituted by lower alkyl substituted by one or more halogens.

In another particular embodiment of the present invention, the compounds have a structure according to formula I or IA, whereby $R^1$ is —$NR^2R^3$; and $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens.

In another particular embodiment of the present invention, the compounds have a structure according to formula I or IA, wherein $R^1$ is lower alkyl and Ar is phenyl.

In another particular embodiment of the present invention, the compounds have a structure according to formula I or IA, wherein $R^1$ is lower alkyl; Ar is phenyl and X is $(CH_2)_2$.

In a particular embodiment of the invention, the compounds have a structure of formula I or IA, whereby $R^1$ is —$NR^2R^3$; and Ar is phenyl.

In a particular embodiment of the invention, the compounds have a structure of formula I or IA, whereby $R^1$ is —$NR^2R^3$; Ar is phenyl and $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens.

In a particular embodiment of the invention, the compounds have a structure of formula I or IA, whereby $R^1$ is —$NR^2R^3$; X is —$(CH_2)_2$— and $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens.

In a particular embodiment of the invention, the compounds have a structure of formula I or IA, whereby $R^1$ is —$NR^2R^3$; Ar is phenyl; $R^2$ and $R^3$ form together with the N-atom to which they are attached a heterocycloalkyl group with 4 or 5 carbon atoms, which is optionally substituted by one or more substituents selected from halogen; or lower alkyl substituted by one or more halogens; and X is —$(CH_2)_2$.

In a particular embodiment, the present invention relates to the following compounds, uses, medicaments and processes:

The present compounds are useful for treating certain neurodegenerative disorders characterized by cytotoxic TAU misfolding and/or aggregation in order to delay or halt the progression of such diseases. Such diseases are summarized under the term tauopathy. The term "Tauopathy" refers to a disease characterised by dysfunctioning and/or toxicity of the TAU protein, characterised by oligomers, aggregates or polymers of said protein. Such diseases include, but are not limited to, Alzheimer's disease, Pick's disease, corticobasal degeneration, progressive supranuclear palsy, frontotemporal dementia and parkinsonism (linked to chromosome 17, FTDP-17).

Tauopathies are characterised by insoluble aggregates or polymers of hyperphosphorylated TAU which are formed by self-polymerisation of TAU monomers. The precise molecular mechanisms involved in TAU aggregation are not precisely known, but may involve a partial denaturation or misfolding of TAU in conformations which have a high propensity to self-organise into higher order structures. The misfolding and aggregation may be triggered by hyperphosphorylation of TAU, although at present it cannot be excluded that such aberrant phosphorylation is a consequence rather than the cause of aggregation.

TAU is a protein with the ability to bind—and consequently stabilise and define—microtubule structure and function in neurons. The binding of TAU to microtubules is regulated by phosphorylation of TAU and several TAU phosphorylation sites and their corresponding kinases have been identified which control phosphorylation status of TAU and consequently modulate the affinity of TAU-binding to microtubules.

An important aspect of the TAU aggregation is its associated cytotoxicity which reduces neuronal integrity and functionality and ultimately resulting in disease symptoms. A direct role of TAU in disease onset has been established unequivocally by the elucidation of familial mutations in TAU which appear to be responsible for a very early and sometimes aggressive form of tauopathy. Such mutations comprise changes in the amino acid sequence of TAU that—directly or indirectly—promote neurotoxic aggregation.

Alzheimer's disease (AD) is the best known of these, where TAU protein is deposited within neurons in the form of neurofibrillary tangles (NFTs). They were first described by the eponymous Alois Alzheimer in one of his patients suffering from the disorder. The term "Alzheimer's disease" as used herein, refers to a chronic progressive nervous disease characterised by neurodegeneration with as most important (early) symptom being memory loss. As the disease advances, symptoms may include confusion, irritability and aggression, mood swings, language breakdown, long-term memory loss, and the general withdrawal of the sufferer as their senses decline.

Tangles are formed by hyperphosphorylation of a microtubule-associated protein known as TAU, causing it to aggregate in an insoluble form. (These aggregations of hyperphosphorylated TAU protein are also referred to as PHF, or "paired helical filaments"). The precise mechanism of tangle formation is not completely understood, and it is still controversial whether tangles are a primary causative factor in the disease or play a more peripheral role. AD is also classified as an amyloidosis because of the presence of senile plaques.

Other conditions in which neurofibrillary tangles are commonly observed include: progressive supranuclear palsy, dementia pugilistica (chronic traumatic encephalopathy), frontotemporal dementia and parkinsonism linked to chromosome 17, Lytico-Bodig disease (Parkinson-dementia complex of Guam), tangle-predominant dementia with NFTs, similar to AD, but without plaques, ganglioglioma and gangliocytoma, meningioangiomatosis, subacute sclerosing panencephalitis, tuberous sclerosis, Hallervorden-Spatz disease, and lipofuscinosis.

The non-Alzheimer's tauopathies are sometimes grouped together as "Pick's complex". In Pick's disease and corticobasal degeneration tau proteins are deposited in the form of inclusion bodies within swollen or "ballooned" neurons. Argyrophilic grain disease (AGD), another type of dementia, is marked by the presence of abundant argyrophilic grains and coiled bodies on microscopic examination of brain tissue.

Similar compounds as described in formula IA and I of the present invention have been described in WO2007/090617.

In comparison with the findings in WO2007/090617, it has been found that there was a marked decrease of the clearance (Clint) and lipophilicity, in particular in the human in-vitro microsomes assay. It is very important for a drug to have a moderate or low clearance and lipophilicity, as this often leads to a higher oral bioavailability. Reducing the clearance and lipophilicity of a compound/drug could then potentially reduce drastically the daily dose required for efficacy and therefore give also a much better safety profile as well. Therefore a low clearance and lipophilicity is an essential feature for therapeutic applicability.

The following examples in table I below highlight these finding, where the use of compounds of formula I and IA have led to compounds with a lower clearance (Clint) and lipophilicity.

Lipophilicity data were measured with the Carrier mediated distribution system (CAMDIS) as described in EP1705474A1.

Microsomal Stability Testing—Assay Description

The microsomal stability assay measures the rate of disappearance of a test compound from an incubation containing human or animal liver microsomes and metabolic cofactors (typically NADPH). The assay is primarily used for ranking the relative CYP-mediated metabolism propensities of compounds within a chemical series and as a guide to selecting sufficiently stable compounds for pharmacokinetics and pharmacodynamics experiments. [In addition to CYPs, microsomally located enzymes which also make use of NADPH (such as flavone mono-oxygenases) and those which require no cofactors (such as carboxylesterases) are active.]

Incubations are performed in 96-well deep-well plates with a final incubation volume of 600 µL. Incubations contain (finally) 1-2 µM test compound, 0.5 mg/mL liver microsomes (typically human, rat or mouse) and NADPH regenerating system. 50 µL aliquots are removed after 1, 3, 6, 9, 15, 25, 35 and 45 minutes and quenched in 150 µL acetonitrile containing internal standard. Samples are then cooled and centrifuged before analysis by LC-MS/MS.

Log peak area ratio (test compound peak area/internal standard peak area) is plotted against incubation time and a linear fit made to the data with emphasis upon the initial rate of compound disappearance. The slope of the fit is then used to calculate the intrinsic clearance:

$$Cl_{int}(\mu L/min/mg) = -slope(min^{-1}) * 1000/[protein\ concentration]$$

TABLE I

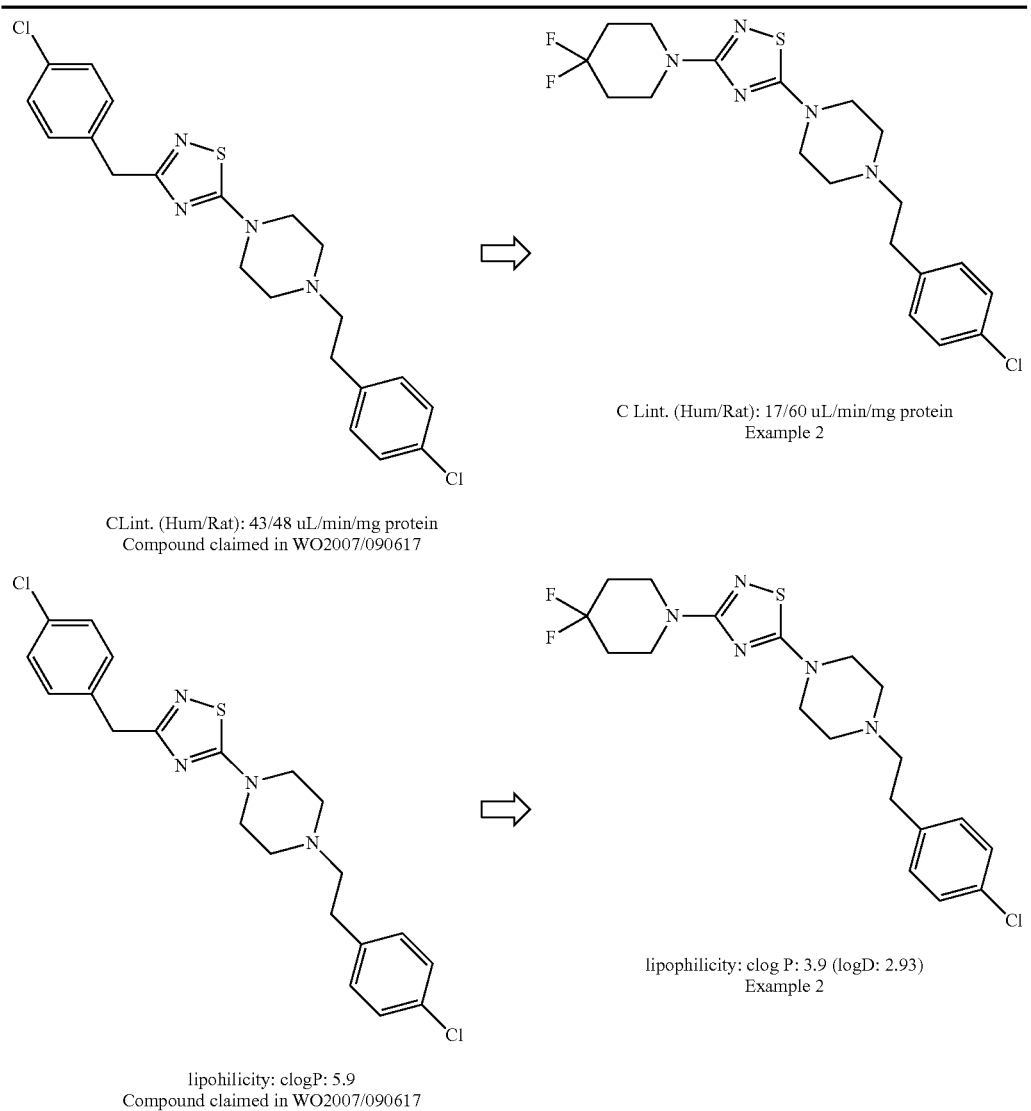

CLint. (Hum/Rat): 43/48 uL/min/mg protein
Compound claimed in WO2007/090617

C Lint. (Hum/Rat): 17/60 uL/min/mg protein
Example 2 lipohilicity: clogP: 5.9
Compound claimed in WO2007/090617 lipophilicity: clog P: 3.9 (logD: 2.93)
Example 2

As it can be seen in the table above, it has been found a marked increase of metabolic stability in particular in human in vitro microsomes.

Objects of the present invention are new compounds of formula I and IA and their pharmaceutically acceptable salts, their use for the treatment of diseases related to the biological function of dysfunction of TAU protein, which diseases comprise Alzheimer's disease, Pick's disease, corticobasal degeneration, progressive supranuclear palsy, frontotemporal dementia and parkinsonism (linked to chromosome 17, FTDP-17), their manufacture and medicaments based on a compound in accordance with the invention in the control or prevention of illnesses.

The preferred indication using the compounds of the present invention is Alzheimer's disease.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-6 carbon atoms. More preferred alkyl groups are groups with 1-4 carbon atoms.

As used herein, the term "lower alkyl substituted by one or more halogens" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

The term "halogen" denotes chlorine, iodine, fluorine and bromine.

The term "cycloalkyl" is an alkylene ring, containing from 3 to 6 carbon ring atoms. Preferred is cyclopropyl or cyclohexyl.

The term "$R^2$ and $R^3$ form together with the N-atom to which they are attached a heterocycloalkyl group with 4 or 5 carbon atoms" denotes a heterocyclyl ring, which contain at least one N-atom in 1-position, for example piperidin-1-yl or pyrrolidin-1-yl.

As used herein, the term "lower alkoxy" denotes a group wherein the alkyl residue is as defined above and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

One embodiment of the invention are compounds of formula IA, wherein X is —(CH$_2$)$_2$—, for example the following compounds 1-[3-(4,4-Difluoro-piperidin-1-yl)-[1,2,4]thiadiazol-5-yl]-4-[2-(4-methoxy-phenyl)-ethyl]-piperazine
1-[2-(4-Chloro-phenyl)-ethyl]-4-[3-(4,4-difluoro-piperidin-1-yl)-[1,2,4]thiadiazol-5-yl]-piperazine
1-[2-(4-Chloro-phenyl)-ethyl]-4-[3-(3,3-difluoro-pyrrolidin-1-yl)-[1,2,4]thiadiazol-5-yl]-piperazine
1-[2-(4-Chloro-phenyl)-ethyl]-4-[3-(4-fluoro-piperidin-1-yl)-[1,2,4]thiadiazol-5-yl]-piperazine
1-[2-(4-Chloro-phenyl)-ethyl]-4-[3-(4-trifluoromethyl-piperidin-1-yl)-[1,2,4]thiadiazol-5-yl]-piperazine
1-[2-(4-Chloro-phenyl)-ethyl]-4-(3-piperidin-1-yl-[1,2,4]thiadiazol-5-yl)-piperazine
(5-{4-[2-(4-Chloro-phenyl)-ethyl]-piperazin-1-yl}-[1,2,4]thiadiazol-3-yl)-cyclopropylmethyl-amine
(5-{4-[2-(4-Chloro-phenyl)-ethyl]-piperazin-1-yl}-[1,2,4]thiadiazol-3-yl)-(tetrahydro-pyran-4-yl)-amine
(5-{4-[2-(4-Chloro-phenyl)-ethyl]-piperazin-1-yl}-[1,2,4]thiadiazol-3-yl)-cyclohexyl-amine
1-[2-(3,4-Difluoro-phenyl)-ethyl]-4-[3-(4,4-difluoro-piperidin-1-yl)-[1,2,4]thiadiazol-5-yl]-piperazine
1-[2-(3,4-Difluoro-phenyl)-ethyl]-4-[3-(3,3-difluoro-pyrrolidin-1-yl)-[1,2,4]thiadiazol-5-yl]-piperazine
1-[2-(3,4-Difluoro-phenyl)-ethyl]-4-[3-(4-fluoro-piperidin-1-yl)-[1,2,4]thiadiazol-5-yl]-piperazine
1-[2-(3,4-Difluoro-phenyl)-ethyl]-4-[3-(4-trifluoromethyl-piperidin-1-yl)-[1,2,4]thiadiazol-5-yl]-piperazine
1-[2-(3,4-Difluoro-phenyl)-ethyl]-4-(3-pyrrolidin-1-yl-[1,2,4]thiadiazol-5-yl)-piperazine
Cyclopropylmethyl-(5-{4-[2-(3,4-difluoro-phenyl)-ethyl]-piperazin-1-yl}-[1,2,4]thiadiazol-3-yl)-amine
(5-{4-[2-(3,4-Difluoro-phenyl)-ethyl]-piperazin-1-yl}-[1,2,4]thiadiazol-3-yl)-(tetrahydro-pyran-4-yl)-amine
Cyclohexyl-(5-{4-[2-(3,4-difluoro-phenyl)-ethyl]-piperazin-1-yl}-[1,2,4]thiadiazol-3-yl)-amine
1-[2-(3,4-Difluoro-phenyl)-ethyl]-4-(3-piperidin-1-yl-[1,2,4]thiadiazol-5-yl)-piperazine
(5-{4-[2-(3,4-Difluoro-phenyl)-ethyl]-piperazin-1-yl}-[1,2,4]thiadiazol-3-yl)-(4-trifluoromethyl-cyclohexyl)-amine
Butyl-(5-{4-[2-(3,4-difluoro-phenyl)-ethyl]-piperazin-1-yl}-[1,2,4]thiadiazol-3-yl)-ethyl-amine
1-(3-Cyclohexyl-[1,2,4]thiadiazol-5-yl)-4-[2-(4-methoxy-phenyl)-ethyl]-piperazine
1-(3-Cyclohexyl-[1,2,4]thiadiazol-5-yl)-4-[2-(3-methoxy-phenyl)-ethyl]-piperazine
1-(3-Butyl-[1,2,4]thiadiazol-5-yl)-4-[2-(4-methoxy-phenyl)-ethyl]-piperazine
1-(3-Cyclopropyl-[1,2,4]thiadiazol-5-yl)-4-[2-(4-methoxy-phenyl)-ethyl]-piperazine
1-(3-Butyl-[1,2,4]thiadiazol-5-yl)-4-[2-(3-methoxy-phenyl)-ethyl]-piperazine
1-(3-Cyclopropyl-[1,2,4]thiadiazol-5-yl)-4-[2-(3-methoxy-phenyl)-ethyl]-piperazine
1-[2-(4-Fluoro-phenyl)-ethyl]-4-[3-(tetrahydro-pyran-4-yl)-[1,2,4]thiadiazol-5-yl]-piperazine
1-[2-(4-Methoxy-phenyl)-ethyl]-4-[3-(tetrahydro-pyran-4-yl)-[1,2,4]thiadiazol-5-yl]-piperazine
1-[2-(2-Methoxy-pyridin-4-yl)-ethyl]-4-[3-(tetrahydro-pyran-4-yl)-[1,2,4]thiadiazol-5-yl]-piperazine
1-[2-(3,4-Difluoro-phenyl)-ethyl]-4-[3-(tetrahydro-pyran-4-yl)-[1,2,4]thiadiazol-5-yl]-piperazine
3-((3-chlorophenoxy)methyl)-5-(4-(3-methoxyphenethyl)piperazin-1-yl)-1,2,4-thiadiazole
3-(2-(benzyloxy)ethyl)-5-(4-(3-methoxyphenethyl)piperazin-1-yl)-1,2,4-thiadiazole
3-((4-fluorophenoxy)methyl)-5-(4-(3-methoxyphenethyl)piperazin-1-yl)-1,2,4-thiadiazole or
3-((4-fluorophenoxy)methyl)-5-(4-(4-methoxyphenethyl)piperazin-1-yl)-1,2,4-thiadiazole.

One embodiment of the invention are compounds of formula IA wherein X is —(CH$_2$)$_2$— and G$^1$ is selected from: lower alkyl; cycloalkyl; tetrahydropyran-4-yl; phenoxymethyl substituted by halogen or benzyloxy-ethyl substituted by halogen, for example the compounds 1-(3-Cyclohexyl-[1,2,4]thiadiazol-5-yl)-4-[2-(4-methoxy-phenyl)-ethyl]-piperazine
1-(3-Cyclohexyl-[1,2,4]thiadiazol-5-yl)-4-[2-(3-methoxy-phenyl)-ethyl]-piperazine
1-(3-Butyl-[1,2,4]thiadiazol-5-yl)-4-[2-(4-methoxy-phenyl)-ethyl]-piperazine
1-(3-Cyclopropyl-[1,2,4]thiadiazol-5-yl)-4-[2-(4-methoxy-phenyl)-ethyl]-piperazine
1-(3-Butyl-[1,2,4]thiadiazol-5-yl)-4-[2-(3-methoxy-phenyl)-ethyl]-piperazine
1-(3-Cyclopropyl-[1,2,4]thiadiazol-5-yl)-4-[2-(3-methoxy-phenyl)-ethyl]-piperazine
1-[2-(4-Fluoro-phenyl)-ethyl]-4-[3-(tetrahydro-pyran-4-yl)-[1,2,4]thiadiazol-5-yl]-piperazine
1-[2-(4-Methoxy-phenyl)-ethyl]-4-[3-(tetrahydro-pyran-4-yl)-[1,2,4]thiadiazol-5-yl]-piperazine
1-[2-(2-Methoxy-pyridin-4-yl)-ethyl]-4-[3-(tetrahydro-pyran-4-yl)-[1,2,4]thiadiazol-5-yl]-piperazine
1-[2-(3,4-Difluoro-phenyl)-ethyl]-4-[3-(tetrahydro-pyran-4-yl)-[1,2,4]thiadiazol-5-yl]-piperazine
3-((3-chlorophenoxy)methyl)-5-(4-(3-methoxyphenethyl)piperazin-1-yl)-1,2,4-thiadiazole
3-(2-(benzyloxy)ethyl)-5-(4-(3-methoxyphenethyl)piperazin-1-yl)-1,2,4-thiadiazole
3-((4-fluorophenoxy)methyl)-5-(4-(3-methoxyphenethyl)piperazin-1-yl)-1,2,4-thiadiazole or
3-((4-fluorophenoxy)methyl)-5-(4-(4-methoxyphenethyl)piperazin-1-yl)-1,2,4-thiadiazole.

One further embodiment of the invention are compounds of formula IA wherein X is —(CH$_2$)$_2$— and G$^1$ is —NR$^2$R$^3$.

One further embodiment of the invention are compounds of formula IA wherein X is —(CH$_2$)$_2$— and G$^1$ is —NR$^2$R$^3$, R$^2$ is hydrogen and R$^3$ is lower alkyl, tetrahydropyran-4-yl, —CH$_2$-cycloalkyl or cycloalkyl optionally substituted by lower alkyl substituted by one or more halogens, for example the compounds (5-{4-[2-(4-Chloro-phenyl)-ethyl]-piperazin-1-yl}-[1,2,4]thiadiazol-3-yl)-cyclopropylmethyl-amine
(5-{4-[2-(4-Chloro-phenyl)-ethyl]-piperazin-1-yl}-[1,2,4]thiadiazol-3-yl)-(tetrahydro-pyran-4-yl)-amine
(5-{4-[2-(4-Chloro-phenyl)-ethyl]-piperazin-1-yl}-[1,2,4]thiadiazol-3-yl)-cyclohexyl-amine
Cyclopropylmethyl-(5-{4-[2-(3,4-difluoro-phenyl)-ethyl]-piperazin-1-yl}-[1,2,4]thiadiazol-3-yl)-amine
(5-{4-[2-(3,4-Difluoro-phenyl)-ethyl]-piperazin-1-yl}-[1,2,4]thiadiazol-3-yl)-(tetrahydro-pyran-4-yl)-amine
Cyclohexyl-(5-{4-[2-(3,4-difluoro-phenyl)-ethyl]-piperazin-1-yl}-[1,2,4]thiadiazol-3-yl)-amine or
(5-{4-[2-(3,4-Difluoro-phenyl)-ethyl]-piperazin-1-yl}-[1,2,4]thiadiazol-3-yl)-(4-trifluoromethyl-cyclohexyl)-amine One further embodiment of the invention are compounds of formula IA wherein X is —(CH$_2$)$_2$— and G$^1$ is —NR$^2$R$^3$, and R² and R³ form together with the N-atom to which they are attached, a heterocycloalkyl group with 4 or 5 carbon atoms, which is optionally substituted by one or more substituents selected from halogen or lower alkyl substituted by one or more halogens, for example the compounds 1-[3-(4,4-Difluoro-piperidin-1-yl)-[1,2,4]thiadiazol-5-yl]-4-[2-(4-methoxy-phenyl)-ethyl]-piperazine 1-[2-(4-Chloro-phenyl)-ethyl]-4-[3-(4,4-difluoro-piperidin-1-yl)-[1,2,4]thiadiazol-5-yl]-piperazine 1-[2-(4-Chloro-phenyl)-ethyl]-4-[3-(3,3-difluoro-pyrrolidin-1-yl)-[1,2,4]thiadiazol-5-yl]-piperazine 1-[2-(4-Chloro-phenyl)-ethyl]-4-[3-(4-fluoro-piperidin-1-yl)-[1,2,4]thiadiazol-5-yl]-piperazine 1-[2-(4-Chloro-phenyl)-ethyl]-4-[3-(4-trifluoromethyl-piperidin-1-yl)-[1,2,4]thiadiazol-5-yl]-piperazine 1-[2-(4-Chloro-phenyl)-ethyl]-4-(3-piperidin-1-yl-[1,2,4]thiadiazol-5-yl)-piperazine 1-[2-(3,4-Difluoro-phenyl)-ethyl]-4-[3-(4,4-difluoro-piperidin-1-yl)-[1,2,4]thiadiazol-5-yl]-piperazine 1-[2-(3,4-Difluoro-phenyl)-ethyl]-4-[3-(3,3-difluoro-pyrrolidin-1-yl)-[1,2,4]thiadiazol-5-yl]-piperazine 1-[2-(3,4-Difluoro-phenyl)-ethyl]-4-[3-(4-fluoro-piperidin-1-yl)-[1,2,4]thiadiazol-5-yl]-piperazine 1-[2-(3,4-Difluoro-phenyl)-ethyl]-4-[3-(4-trifluoromethyl-piperidin-1-yl)-[1,2,4]thiadiazol-5-yl]-piperazine 1-[2-(3,4-Difluoro-phenyl)-ethyl]-4-(3-pyrrolidin-1-yl-[1,2,4]thiadiazol-5-yl)-piperazine 1-[2-(3,4-Difluoro-phenyl)-ethyl]-4-(3-piperidin-1-yl-[1,2,4]thiadiazol-5-yl)-piperazine One further embodiment of the invention are compounds of formula IA, wherein X is —CH₂—, for example the compounds 1-(2-Methyl-benzyl)-4-[3-(tetrahydro-pyran-4-yl)-[1,2,4]thiadiazol-5-yl]-piperazine or 3-(4-chlorophenethyl)-5-(4-(2-methylbenzyl)piperazin-1-yl)-1,2,4-thiadiazole.

One embodiment of the invention are compounds of formula I, wherein X is —(CH₂)₂—, for example the following compounds: 1-[3-(4,4-Difluoro-piperidin-1-yl)-[1,2,4]thiadiazol-5-yl]-4-[2-(4-methoxy-phenyl)-ethyl]-piperazine; 1-[2-(4-Chloro-phenyl)-ethyl]-4-[3-(4,4-difluoro-piperidin-1-yl)-[1,2,4]thiadiazol-5-yl]-piperazine; 1-[2-(4-Chloro-phenyl)-ethyl]-4-[3-(3,3-difluoro-pyrrolidin-1-yl)-[1,2,4]thiadiazol-5-yl]-piperazine; 1-[2-(4-Chloro-phenyl)-ethyl]-4-[3-(4-fluoro-piperidin-1-yl)-[1,2,4]thiadiazol-5-yl]-piperazine; 1-[2-(4-Chloro-phenyl)-ethyl]-4-[3-(4-trifluoromethyl-piperidin-1-yl)-[1,2,4]thiadiazol-5-yl]-piperazine; 1-[2-(4-Chloro-phenyl)-ethyl]-4-(3-piperidin-1-yl-[1,2,4]thiadiazol-5-yl)-piperazine; (5-{4-[2-(4-Chloro-phenyl)-ethyl]-piperazin-1-yl}-[1,2,4]thiadiazol-3-yl)-cyclopropylmethyl-amine; (5-{4-[2-(4-Chloro-phenyl)-ethyl]-piperazin-1-yl}-[1,2,4]thiadiazol-3-yl)-(tetrahydro-pyran-4-yl)-amine; (5-{4-[2-(4-Chloro-phenyl)-ethyl]-piperazin-1-yl}-[1,2,4]thiadiazol-3-yl)-cyclohexyl-amine; 1-[2-(3,4-Difluoro-phenyl)-ethyl]-4-[3-(4,4-difluoro-piperidin-1-yl)-[1,2,4]thiadiazol-5-yl]-piperazine; 1-[2-(3,4-Difluoro-phenyl)-ethyl]-4-[3-(3,3-difluoro-pyrrolidin-1-yl)-[1,2,4]thiadiazol-5-yl]-piperazine; 1-[2-(3,4-Difluoro-phenyl)-ethyl]-4-[3-(4-fluoro-piperidin-1-yl)-[1,2,4]thiadiazol-5-yl]-piperazine; 1-[2-(3,4-Difluoro-phenyl)-ethyl]-4-[3-(4-trifluoromethyl-piperidin-1-yl)-[1,2,4]thiadiazol-5-yl]-piperazine; 1-[2-(3,4-Difluoro-phenyl)-ethyl]-4-(3-pyrrolidin-1-yl-[1,2,4]thiadiazol-5-yl)-piperazine; Cyclopropylmethyl-(5-{4-[2-(3,4-difluoro-phenyl)-ethyl]-piperazin-1-yl}-[1,2,4]thiadiazol-3-yl)-amine; (5-{4-[2-(3,4-Difluoro-phenyl)-ethyl]-piperazin-1-yl}-[1,2,4]thiadiazol-3-yl)-(tetrahydro-pyran-4-yl)-amine; Cyclohexyl-(5-{4-[2-(3,4-difluoro-phenyl)-ethyl]-piperazin-1-yl}-[1,2,4]thiadiazol-3-yl)-amine; 1-[2-(3,4-Difluoro-phenyl)-ethyl]-4-(3-piperidin-1-yl-[1,2,4]thiadiazol-5-yl)-piperazine; (5-{4-[2-(3,4-Difluoro-phenyl)-ethyl]-piperazin-1-yl}-[1,2,4]thiadiazol-3-yl)-(4-trifluoromethyl-cyclohexyl)-amine; Butyl-(5-{4-[2-(3,4-difluoro-phenyl)-ethyl]-piperazin-1-yl}-[1,2,4]thiadiazol-3-yl)-ethyl-amine; 1-(3-Cyclohexyl-[1,2,4]thiadiazol-5-yl)-4-[2-(4-methoxy-phenyl)-ethyl]-piperazine; 1-(3-Cyclohexyl-[1,2,4]thiadiazol-5-yl)-4-[2-(3-methoxy-phenyl)-ethyl]-piperazine; 1-(3-Butyl-[1,2,4]thiadiazol-5-yl)-4-[2-(4-methoxy-phenyl)-ethyl]-piperazine; 1-(3-Cyclopropyl-[1,2,4]thiadiazol-5-yl)-4-[2-(4-methoxy-phenyl)-ethyl]-piperazine; 1-(3-Butyl-[1,2,4]thiadiazol-5-yl)-4-[2-(3-methoxy-phenyl)-ethyl]-piperazine; 1-(3-Cyclopropyl-[1,2,4]thiadiazol-5-yl)-4-[2-(3-methoxy-phenyl)-ethyl]-piperazine; 1-[2-(4-Fluoro-phenyl)-ethyl]-4-[3-(tetrahydro-pyran-4-yl)-[1,2,4]thiadiazol-5-yl]-piperazine; 1-[2-(4-Methoxy-phenyl)-ethyl]-4-[3-(tetrahydro-pyran-4-yl)-[1,2,4]thiadiazol-5-yl]-piperazine; 1-[2-(2-Methoxy-pyridin-4-yl)-ethyl]-4-[3-(tetrahydro-pyran-4-yl)-[1,2,4]thiadiazol-5-yl]-piperazine or 1-[2-(3,4-Difluoro-phenyl)-ethyl]-4-[3-(tetrahydro-pyran-4-yl)-[1,2,4]thiadiazol-5-yl]-piperazine.

One further embodiment of the invention are compounds of formula I, wherein R¹ is lower alkyl, cycloalkyl or tetrahydropyran-4-yl, for example the following compounds: 1-(3-Cyclohexyl-[1,2,4]thiadiazol-5-yl)-4-[2-(4-methoxy-phenyl)-ethyl]-piperazine; 1-(3-Cyclohexyl-[1,2,4]thiadiazol-5-yl)-4-[2-(3-methoxy-phenyl)-ethyl]-piperazine; 1-(3-Butyl-[1,2,4]thiadiazol-5-yl)-4-[2-(4-methoxy-phenyl)-ethyl]-piperazine; 1-(3-Cyclopropyl-[1,2,4]thiadiazol-5-yl)-4-[2-(4-methoxy-phenyl)-ethyl]-piperazine; 1-(3-Butyl-[1,2,4]thiadiazol-5-yl)-4-[2-(3-methoxy-phenyl)-ethyl]-piperazine; 1-(3-Cyclopropyl-[1,2,4]thiadiazol-5-yl)-4-[2-(3-methoxy-phenyl)-ethyl]-piperazine; 1-[2-(4-Fluoro-phenyl)-ethyl]-4-[3-(tetrahydro-pyran-4-yl)-[1,2,4]thiadiazol-5-yl]-piperazine; 1-[2-(4-Methoxy-phenyl)-ethyl]-4-[3-(tetrahydro-pyran-4-yl)-[1,2,4]thiadiazol-5-yl]-piperazine; 1-[2-(2-Methoxy-pyridin-4-yl)-ethyl]-4-[3-(tetrahydro-pyran-4-yl)-[1,2,4]thiadiazol-5-yl]-piperazine; or 1-[2-(3,4-Difluoro-phenyl)-ethyl]-4-[3-(tetrahydro-pyran-4-yl)-[1,2,4]thiadiazol-5-yl]-piperazine.

One further embodiment of the invention are compounds of formula I, wherein R² is hydrogen and R³ is lower alkyl, tetrahydropyran-4-yl, —CH₂-cycloalkyl or cycloalkyl optionally substituted by lower alkyl substituted by one or more halogens, for example the following compounds: (5-{4-[2-(4-Chloro-phenyl)-ethyl]-piperazin-1-yl}-[1,2,4]thiadiazol-3-yl)-cyclopropylmethyl-amine; (5-{4-[2-(4-Chloro-phenyl)-ethyl]-piperazin-1-yl}-[1,2,4]thiadiazol-3-yl)-(tetrahydro-pyran-4-yl)-amine; (5-{4-[2-(4-Chloro-phenyl)-ethyl]-piperazin-1-yl}-[1,2,4]thiadiazol-3-yl)-cyclohexyl-amine; Cyclopropylmethyl-(5-{4-[2-(3,4-difluoro-phenyl)-ethyl]-piperazin-1-yl}-[1,2,4]thiadiazol-3-yl)-amine; (5-{4-[2-(3,4-Difluoro-phenyl)-ethyl]-piperazin-1-yl}-[1,2,4]thiadiazol-3-yl)-(tetrahydro-pyran-4-yl)-amine; Cyclohexyl-(5-{4-[2-(3,4-difluoro-phenyl)-ethyl]-piperazin-1-yl}-[1,2,4]thiadiazol-3-yl)-amine; or (5-{4-[2-(3,4-Difluoro-phenyl)-ethyl]-piperazin-1-yl}-[1,2,4]thiadiazol-3-yl)-(4-trifluoromethyl-cyclohexyl)-amine One further embodiment of the invention are compounds of formula I, wherein R² and R³ form together with the N-atom to which they are attached a heterocycloalkyl group with 4 or 5 carbon atoms, which is optionally substituted by one or more substituents selected from halogen or lower alkyl substituted by one or more halogens, for example compounds: 1-[3-(4,4-Difluoro-piperidin-1-yl)-[1,2,4]thiadiazol-5-yl]-4-[2-(4-methoxy-phenyl)-ethyl]-piperazine; 1-[2-

(4-Chloro-phenyl)-ethyl]-4-[3-(4,4-difluoro-piperidin-1-yl)-[1,2,4]thiadiazol-5-yl]-piperazine; 1-[2-(4-Chloro-phenyl)-ethyl]-4-[3-(3,3-difluoro-pyrrolidin-1-yl)-[1,2,4]thiadiazol-5-yl]-piperazine; 1-[2-(4-Chloro-phenyl)-ethyl]-4-[3-(4-fluoro-piperidin-1-yl)-[1,2,4]thiadiazol-5-yl]-piperazine; 1-[2-(4-Chloro-phenyl)-ethyl]-4-[3-(4-trifluoromethyl-piperidin-1-yl)-[1,2,4]thiadiazol-5-yl]-piperazine; 1-[2-(4-Chloro-phenyl)-ethyl]-4-(3-piperidin-1-yl-[1,2,4]thiadiazol-5-yl)-piperazine; 1-[2-(3,4-Difluoro-phenyl)-ethyl]-4-[3-(4,4-difluoro-piperidin-1-yl)-[1,2,4]thiadiazol-5-yl]-piperazine; 1-[2-(3,4-Difluoro-phenyl)-ethyl]-4-[3-(3,3-difluoro-pyrrolidin-1-yl)-[1,2,4]thiadiazol-5-yl]-piperazine; 1-[2-(3,4-Difluoro-phenyl)-ethyl]-4-[3-(4-fluoro-piperidin-1-yl)-[1,2,4]thiadiazol-5-yl]-piperazine; 1-[2-(3,4-Difluoro-phenyl)-ethyl]-4-[3-(4-trifluoromethyl-piperidin-1-yl)-[1,2,4]thiadiazol-5-yl]-piperazine; 1-[2-(3,4-Difluoro-phenyl)-ethyl]-4-(3-pyrrolidin-1-yl-[1,2,4]thiadiazol-5-yl)-piperazine; or 1-[2-(3,4-Difluoro-phenyl)-ethyl]-4-(3-piperidin-1-yl-[1,2,4]thiadiazol-5-yl)-piperazine One further embodiment of the invention are compounds of formula I, wherein $R^2$ is lower alkyl, for example the compound: Butyl-(5-{4-[2-(3,4-difluoro-phenyl)-ethyl]-piperazin-1-yl}-[1,2,4]thiadiazol-3-yl)-ethyl-amine.

The present compounds of formula IA or I and their pharmaceutically acceptable salts can be prepared by methods known in the art, for example, by processes described below, which process comprises
coupling a compound of formula

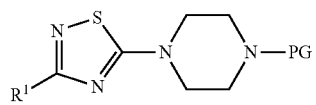

IV with a compound of formula

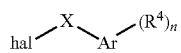

to give a compound of formula

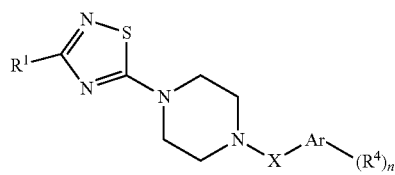

I wherein PG is hydrogen or a protecting group such as tert-butyloxycarbonyl (BOC), 9-fluorenylmethyloxycarbonyl (FMOC) and the like, and hal is halogen such as chloro, bromo, fluoro, or iodo, wherein the definitions are as described above; or if desired, converting the compounds obtained into pharmaceutically acceptable acid addition salts.
In an embodiment, $R^1$ has the same meaning as defined for $G^1$.

General Experimental Part

The preparation of compounds of formula IA or I of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula IA or I can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 2nd Edition*, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1:

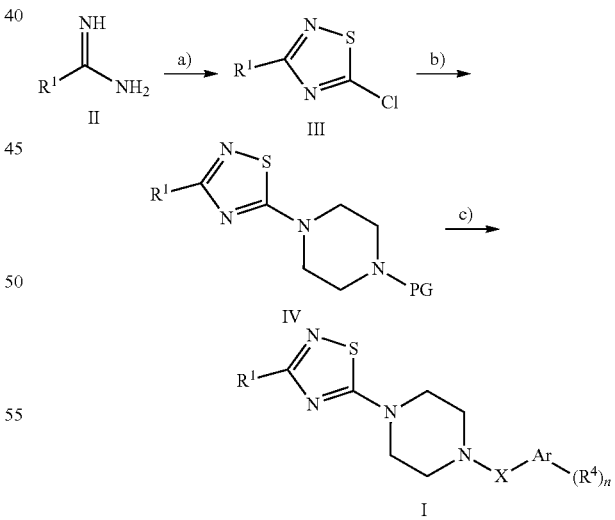

In an embodiment, $R^1$ has the same meaning as defined for $G^1$.

a) Amidines II are either commercially available or can be synthesized according to methods known in the art. These amidine derivatives II are conveniently reacted with perchloromethyl mercaptan with a base (NEt₃, DIPEA and the like) to afford chloro-thiadiazole derivatives III.

b) Chloro-thiadiazole derivatives III are conveniently reacted with either substituted piperazine derivatives to directly access final thiadiazole derivatives I or alternatively III is reacted with a protected piperazine (PG=Boc, and the like) to afford thiadiazole derivatives IV.
c) Deprotection of IV is done under suitable conditions, in case of PG=Boc under acidic conditions, to yield the free piperazine derivatives which are conveniently reacted with suitable electrophiles, such as hal-X—Ar—$(R^4)_n$ to access final thiadiazole derivatives I.

Scheme 2:

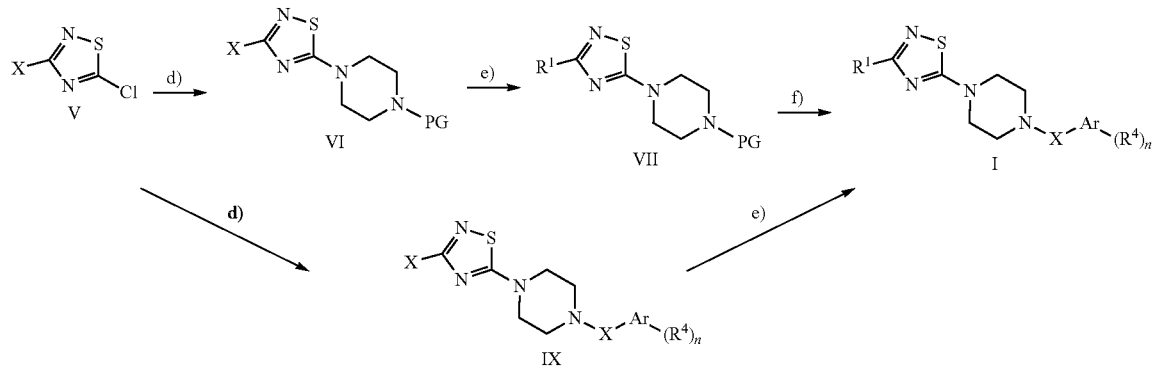

X = Cl or Br d) 3-Bromo-5-chloro-1,2,4-thiadiazole and 3,5-dichloro-1,2,4-thiadiazole V are commercially available and can conveniently be reacted with protected (PG=Boc and the like) or substituted piperazines to yield thiadiazole derivatives VI or IX.
e) Thiadiazole derivatives VI or IX are conveniently reacted with suitable amines to yield in case of IX the final derivatives I or in case of VI the protected thiadiazole derivatives VII.
f) Deprotection of VII is done under suitable conditions, in case of PG=Boc under acidic conditions, to yield the free piperazine derivatives which are conveniently reacted with suitable electrophiles, such as hal-X—Ar—$(R^4)_n$ to access final thiadiazole derivatives I.

EXPERIMENTAL PART

Abbreviations:
DCM=dichloromethane;
DIPEA=N,N-diisopropylethylamine;
EtOH=ethanol;
Et$_3$N=triethylamine;
HPLC=high pressure liquid chromatography;

Exemplary compounds of the present invention are listed in table II

TABLE 2

| Example | Chemical name |
|---|---|
| 1 | 1-[3-(4,4-Difluoro-piperidin-1-yl)-[1,2,4]thiadiazol-5-yl]-4-[2-(4-methoxy-phenyl)-ethyl]-piperazine |
| 2 | 1-[2-(4-Chloro-phenyl)-ethyl]-4-[3-(4,4-difluoro-piperidin-1-yl)-[1,2,4]thiadiazol-5-yl]-piperazine |
| 3 | 1-[2-(4-Chloro-phenyl)-ethyl]-4-[3-(3,3-difluoro-pyrrolidin-1-yl)-[1,2,4]thiadiazol-5-yl]-piperazine |

TABLE 2-continued

| Example | Chemical name |
|---|---|
| 4 | 1-[2-(4-Chloro-phenyl)-ethyl]-4-[3-(4-fluoro-piperidin-1-yl)-[1,2,4]thiadiazol-5-yl]-piperazine |
| 5 | 1-[2-(4-Chloro-phenyl)-ethyl]-4-[3-(4-trifluoromethyl-piperidin-1-yl)-[1,2,4]thiadiazol-5-yl]-piperazine |

TABLE 2-continued

| Example | Chemical name |
|---|---|
| 6 | 1-[2-(4-Chloro-phenyl)-ethyl]-4-(3-piperidin-1-yl-[1,2,4]thiadiazol-5-yl)-piperazine |
| 7 | (5-{4-[2-(4-Chloro-phenyl)-ethyl]-piperazin-1-yl}-[1,2,4]thiadiazol-3-yl)-cyclopropylmethyl-amine |
| 8 | (5-{4-[2-(4-Chloro-phenyl)-ethyl]-piperazin-1-yl}-[1,2,4]thiadiazol-3-yl)-(tetrahydro-pyran-4-yl)-amine |
| 9 | (5-{4-[2-(4-Chloro-phenyl)-ethyl]-piperazin-1-yl}-[1,2,4]thiadiazol-3-yl)-cyclohexyl-amine |
| 10 | 1-[2-(3,4-Difluoro-phenyl)-ethyl]-4-[3-(4,4-difluoro-piperidin-1-yl)-[1,2,4]thiadiazol-5-yl]-piperazine |
| 11 | 1-[2-(3,4-Difluoro-phenyl)-ethyl]-4-[3-(3,3-difluoro-pyrrolidin-1-yl)-[1,2,4]thiadiazol-5-yl]-piperazine |
| 12 | 1-[2-(3,4-Difluoro-phenyl)-ethyl]-4-[3-(4-fluoro-piperidin-1-yl)-[1,2,4]thiadiazol-5-yl]-piperazine |
| 13 | 1-[2-(3,4-Difluoro-phenyl)-ethyl]-4-[3-(4-trifluoromethyl-piperidin-1-yl)-[1,2,4]thiadiazol-5-yl]-piperazine |
| 14 | 1-[2-(3,4-Difluoro-phenyl)-ethyl]-4-(3-pyrrolidin-1-yl-[1,2,4]thiadiazol-5-yl)-piperazine |
| 15 | Cyclopropylmethyl-(5-{4-[2-(3,4-difluoro-phenyl)-ethyl]-piperazin-1-yl}-[1,2,4]thiadiazol-3-yl)-amine |
| 16 | (5-{4-[2-(3,4-Difluoro-phenyl)-ethyl]-piperazin-1-yl}-[1,2,4]thiadiazol-3-yl)-(tetrahydro-pyran-4-yl)-amine |
| 17 | Cyclohexyl-(5-{4-[2-(3,4-difluoro-phenyl)-ethyl]-piperazin-1-yl}-[1,2,4]thiadiazol-3-yl)-amine |
| 18 | 1-[2-(3,4-Difluoro-phenyl)-ethyl]-4-(3-piperidin-1-yl-[1,2,4]thiadiazol-5-yl)-piperazine |
| 19 | (5-{4-[2-(3,4-Difluoro-phenyl)-ethyl]-piperazin-1-yl}-[1,2,4]thiadiazol-3-yl)-(4-trifluoromethyl-cyclohexyl)-amine |
| 20 | Butyl-(5-{4-[2-(3,4-difluoro-phenyl)-ethyl]-piperazin-1-yl}-[1,2,4]thiadiazol-3-yl)-ethyl-amine |
| 21 | 1-(3-Cyclohexyl-[1,2,4]thiadiazol-5-yl)-4-[2-(4-methoxy-phenyl)-ethyl]-piperazine |
| 22 | 1-(3-Cyclohexyl-[1,2,4]thiadiazol-5-yl)-4-[2-(3-methoxy-phenyl)-ethyl]-piperazine |
| 23 | 1-(3-Butyl-[1,2,4]thiadiazol-5-yl)-4-[2-(4-methoxy-phenyl)-ethyl]-piperazine |

TABLE 2-continued

| Example | Chemical name |
|---|---|
| 24 | 1-(3-Cyclopropyl-[1,2,4]thiadiazol-5-yl)-4-[2-(4-methoxy-phenyl)-ethyl]-piperazine |
| 25 | 1-(3-Butyl-[1,2,4]thiadiazol-5-yl)-4-[2-(3-methoxy-phenyl)-ethyl]-piperazine |
| 26 | 1-(3-Cyclopropyl-[1,2,4]thiadiazol-5-yl)-4-[2-(3-methoxy-phenyl)-ethyl]-piperazine |
| 27 | 1-[2-(4-Fluoro-phenyl)-ethyl]-4-[3-(tetrahydro-pyran-4-yl)-[1,2,4]thiadiazol-5-yl]-piperazine |
| 28 | 1-[2-(4-Methoxy-phenyl)-ethyl]-4-[3-(tetrahydro-pyran-4-yl)-[1,2,4]thiadiazol-5-yl]-piperazine |
| 29 | 1-[2-(2-Methoxy-pyridin-4-yl)-ethyl]-4-[3-(tetrahydro-pyran-4-yl)-[1,2,4]thiadiazol-5-yl]-piperazine |
| 30 | 1-(2-Methyl-benzyl)-4-[3-(tetrahydro-pyran-4-yl)-[1,2,4]thiadiazol-5-yl]-piperazine |
| 31 | 1-[2-(3,4-Difluoro-phenyl)-ethyl]-4-[3-(tetrahydro-pyran-4-yl)-[1,2,4]thiadiazol-5-yl]-piperazine |
| 32 | 3-(4-chlorophenethyl)-5-(4-(2-methylbenzyl)piperazin-1-yl)-1,2,4-thiadiazole |
| 33 | 3-((3-chlorophenoxy)methyl)-5-(4-(3-methoxyphenethyl)piperazin-1-yl)-1,2,4-thiadiazole |
| 34 | 3-(2-(benzyloxy)ethyl)-5-(4-(3-methoxyphenethyl)piperazin-1-yl)-1,2,4-thiadiazole |
| 35 | 3-((4-fluorophenoxy)methyl)-5-(4-(3-methoxyphenethyl)piperazin-1-yl)-1,2,4-thiadiazole |
| 36 | 3-((4-fluorophenoxy)methyl)-5-(4-(4-methoxyphenethyl)piperazin-1-yl)-1,2,4-thiadiazole |
| 37 | 5-(4-(4-methoxyphenethyl)piperazin-1-yl)-3-(trifluoromethyl)-1,2,4-thiadiazole |

Example 1

1-[3-(4,4-Difluoro-piperidin-1-yl)-[1,2,4]thiadiazol-5-yl]-4-[2-(4-methoxy-phenyl)-ethyl]-piperazine

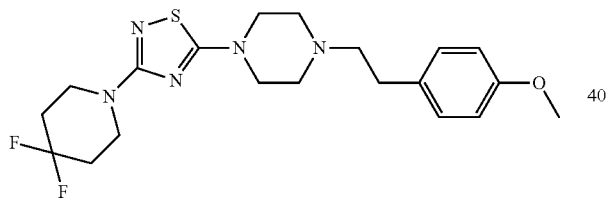

a) 1-(3-Bromo-[1,2,4]thiadiazol-5-yl)-4-[2-(4-methoxy-phenyl)-ethyl]-piperazine

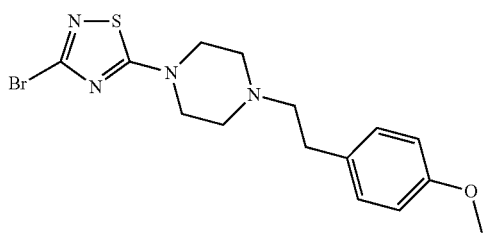 [SMILES: COc1ccc(CCN2CCN(c3nc(Br)ns3)CC2)cc1]

A mixture of 3-bromo-5-chloro-1,2,4-thiadiazole (300 mg, 1.5 mmol), 1-(4-methoxyphenethyl)piperazine dihydrochloride (485 mg, 1.65 mmol) and DIPEA (641 mg, 867 µl, 4.96 mmol) in EtOH (10 mL) was stirred over night at ambient temperature. The mixture was concentrated in vacuo and the residue was purified by silica column chromatography eluting with a gradient formed from heptane and ethyl acetate to yield after evaporation of the product containing fractions 489 mg (85%) of the title compound as off-white solid. MS (m/e): 383.2 (MH$^+$).

b) 1-[3-(4,4-Difluoro-piperidin-1-yl)-[1,2,4]thiadiazol-5-yl]-4-[2-(4-methoxy-phenyl)-ethyl]-piperazine A mixture of 3-bromo-5-(4-(4-methoxyphenethyl)piperazin-1-yl)-1,2,4-thiadiazole (55 mg, 143 µmol), 4,4-difluoropiperidine hydrochloride (67.8 mg, 430 µmol) and DIPEA (185 mg, 251 µl, 1.43 mmol) in N-Methyl-2-pyrrolidinone (1 mL) was heated with microwave at 200° C. for 2.5 h. The amber reaction solution was purified by preparative HPLC on reversed phase eluting with a gradient formed from acetonitrile, water and NEt$_3$ to yield after evaporation of the product containing fractions 41.8 mg (69%) of the title compound as off-white solid. MS (m/e): 424.2 (MH$^+$).

Example 2

1-[2-(4-Chloro-phenyl)-ethyl]-4-[3-(4,4-difluoro-piperidin-1-yl)-[1,2,4]thiadiazol-5-yl]-piperazine

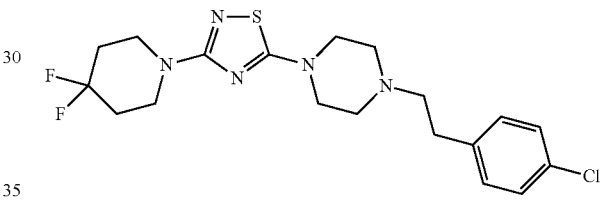

a) 1-(3-Bromo-[1,2,4]thiadiazol-5-yl)-4-[2-(4-chloro-phenyl)-ethyl]-piperazine

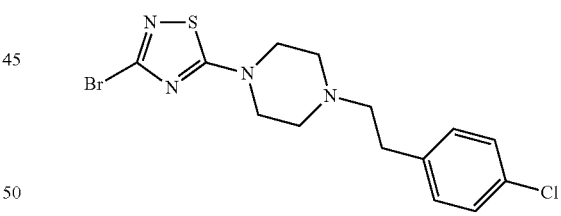

In analogy to the procedure described for the synthesis of 1-(3-bromo-[1,2,4]thiadiazol-5-yl)-4-[2-(4-methoxy-phenyl)-ethyl]-piperazine (example 1, step a) the title compound was prepared from 3-bromo-5-chloro-1,2,4-thiadiazole and 1-(4-chlorophenethyl)piperazine dihydrochloride as white solid. MS (m/e): 389.1 (MH$^+$).

b) 1-[2-(4-Chloro-phenyl)-ethyl]-4-[3-(4,4-difluoro-piperidin-1-yl)-[1,2,4]thiadiazol-5-yl]-piperazine In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]

thiadiazol-5-yl)-4-[2-(4-chloro-phenyl)-ethyl]-piperazine and 4,4-difluoropiperidine hydrochloride. MS (m/e): 428.3 (MH⁺).

Example 3

1-[2-(4-Chloro-phenyl)-ethyl]-4-[3-(3,3-difluoro-pyrrolidin-1-yl)-[1,2,4]thiadiazol-5-yl]-piperazine

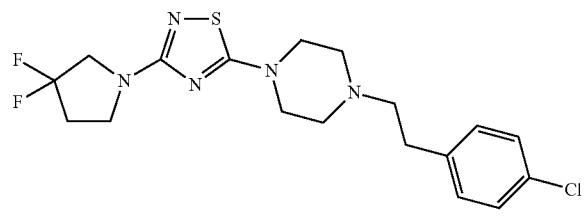 [SMILES: FC1(F)CCN(c2nsc(N3CCN(CCc4ccc(Cl)cc4)CC3)n2)C1]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(4-chloro-phenyl)-ethyl]-piperazine and 3,3-difluoropyrrolidine hydrochloride. MS (m/e): 414.3 (MH⁺).

Example 4

1-[2-(4-Chloro-phenyl)-ethyl]-4-[3-(4-fluoro-piperidin-1-yl)-[1,2,4]thiadiazol-5-yl]-piperazine

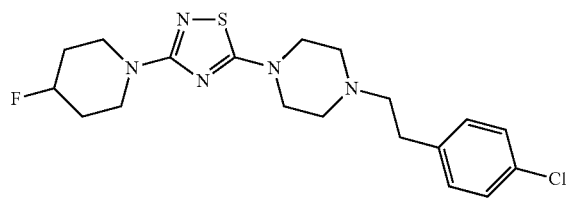 [SMILES: FC1CCN(c2nsc(N3CCN(CCc4ccc(Cl)cc4)CC3)n2)CC1]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(4-chloro-phenyl)-ethyl]-piperazine and 4-fluoropiperidine hydrochloride. MS (m/e): 410.2 (MH⁺).

Example 5

1-[2-(4-Chloro-phenyl)-ethyl]-4-[3-(4-trifluoromethyl-piperidin-1-yl)-[1,2,4]thiadiazol-5-yl]-piperazine

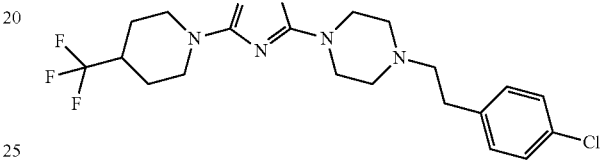

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(4-chloro-phenyl)-ethyl]-piperazine and 4-(trifluoromethyl)piperidine hydrochloride. MS (m/e): 460.2 (MH⁺).

Example 6

1-[2-(4-Chloro-phenyl)-ethyl]-4-(3-piperidin-1-yl-[1,2,4]thiadiazol-5-yl)-piperazine

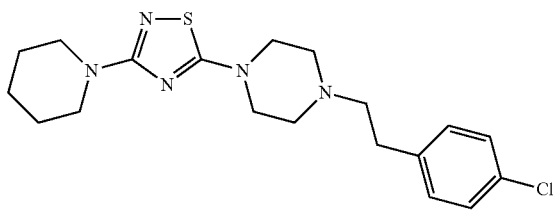 [SMILES: Clc1ccc(CCN2CCN(c3nc(N4CCCCC4)ns3)CC2)cc1]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]

thiadiazol-5-yl)-4-[2-(4-chloro-phenyl)-ethyl]-piperazine and piperidine. MS (m/e): 392.2 (MH+).

Example 7

(5-{4-[2-(4-Chloro-phenyl)-ethyl]-piperazin-1-yl}-[1,2,4]thiadiazol-3-yl)-cyclopropylmethyl-amine

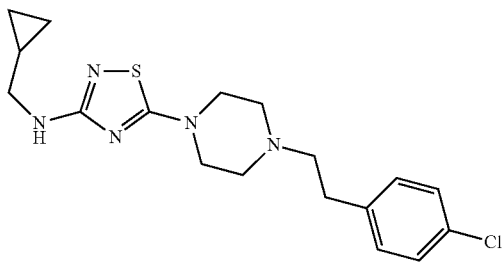 [SMILES: Clc1ccc(CCN2CCN(c3nc(NCC4CC4)ns3)CC2)cc1]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(4-chloro-phenyl)-ethyl]-piperazine and cyclopropylmethanamine. MS (m/e): 378.3 (MH+).

Example 8

(5-{4-[2-(4-Chloro-phenyl)-ethyl]-piperazin-1-yl}-[1,2,4]thiadiazol-3-yl)-(tetrahydro-pyran-4-yl)-amine

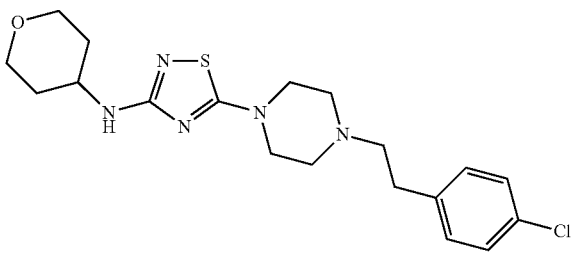 [SMILES: Clc1ccc(CCN2CCN(c3nc(NC4CCCCC4)ns3)CC2)cc1]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4] thiadiazol-5-yl)-4-[2-(4-chloro-phenyl)-ethyl]-piperazine and tetrahydro-2H-pyran-4-amine. MS (m/e): 408.3 (MH+).

Example 9

(5-{4-[2-(4-Chloro-phenyl)-ethyl]-piperazin-1-yl}-[1,2,4]thiadiazol-3-yl)-cyclohexyl-amine

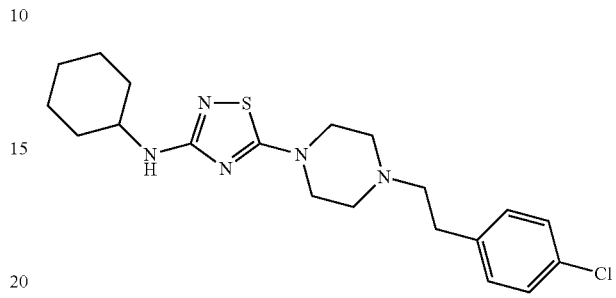

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4] thiadiazol-5-yl)-4-[2-(4-chloro-phenyl)-ethyl]-piperazine and cyclohexanamine. MS (m/e): 406.4 (MH+).

Example 10

1-[2-(3,4-Difluoro-phenyl)-ethyl]-4-[3-(4,4-difluoro-piperidin-1-yl)-[1,2,4]thiadiazol-5-yl]-piperazine

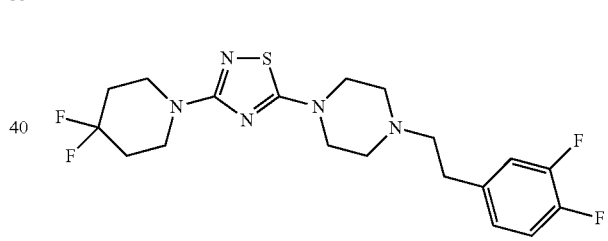

a) 1-(3-Bromo-[1,2,4]thiadiazol-5-yl)-4-[2-(3,4-difluoro-phenyl)-ethyl]-piperazine

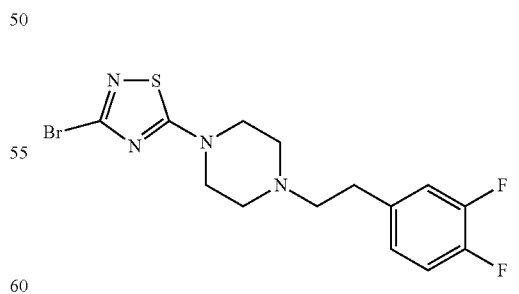

In analogy to the procedure described for the synthesis of 1-(3-Bromo-[1,2,4]thiadiazol-5-yl)-4-[2-(4-methoxy-phenyl)-ethyl]-piperazine (example 1, step a) the title compound was prepared from 3-bromo-5-chloro-1,2,4-thiadiazole and 1-(3,4-difluorophenethyl)piperazine dihydrochloride, as colourless viscous oil. MS (m/e): 391.2 (MH+).

b) 1-[2-(3,4-Difluoro-phenyl)-ethyl]-4-[3-(4,4-difluoro-piperidin-1-yl)-[1,2,4]thiadiazol-5-yl]-piperazine In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(3,4-difluoro-phenyl)-ethyl]-piperazine and 4,4-difluoropiperidine hydrochloride. MS (m/e): 430.3 (MH$^+$).

Example 11

1-[2-(3,4-Difluoro-phenyl)-ethyl]-4-[3-(3,3-difluoro-pyrrolidin-1-yl)-[1,2,4]thiadiazol-5-yl]-piperazine

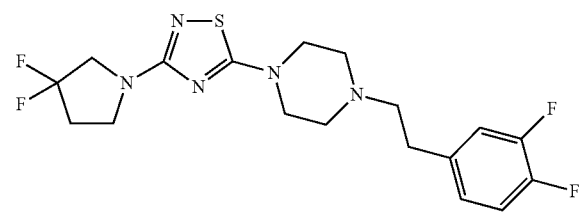 [SMILES: Fc1ccc(CCN2CCN(c3nc(N4CCC(F)(F)C4)ns3)CC2)cc1F]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(3,4-difluoro-phenyl)-ethyl]-piperazine and 3,3-difluoropyrrolidine hydrochloride. MS (m/e): 416.3 (MH$^+$).

Example 12

1-[2-(3,4-Difluoro-phenyl)-ethyl]-4-[3-(4-fluoro-piperidin-1-yl)-[1,2,4]thiadiazol-5-yl]-piperazine

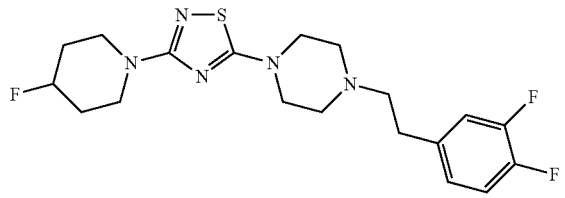 [SMILES: Fc1ccc(CCN2CCN(c3nc(N4CCC(F)CC4)ns3)CC2)cc1F]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(3,4-difluoro-phenyl)-ethyl]-piperazine and 4-fluoropiperidine hydrochloride. MS (m/e): 412.3 (MH$^+$).

Example 13

1-[2-(3,4-Difluoro-phenyl)-ethyl]-4-[3-(4-trifluoromethyl-piperidin-1-yl)-[1,2,4]thiadiazol-5-yl]-piperazine

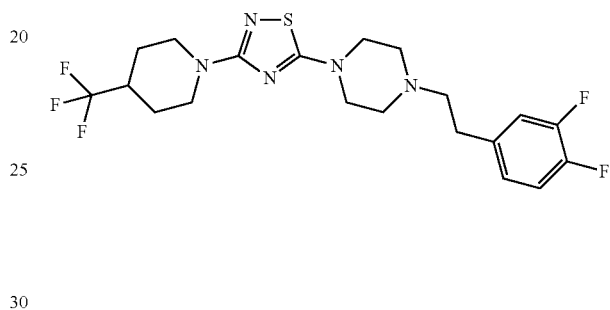

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(3,4-difluoro-phenyl)-ethyl]-piperazine and 4-(trifluoromethyl)piperidine hydrochloride. MS (m/e): 462.3 (MH$^+$).

Example 14

1-[2-(3,4-Difluoro-phenyl)-ethyl]-4-(3-pyrrolidin-1-yl-[1,2,4]thiadiazol-5-yl)-piperazine

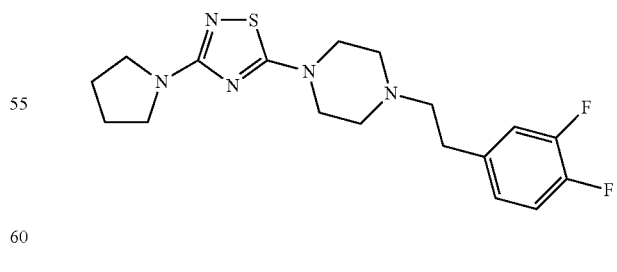

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]

thiadiazol-5-yl)-4-[2-(3,4-difluoro-phenyl)-ethyl]-piperazine and pyrrolidine. MS (m/e): 380.3 (MH+).

Example 15

Cyclopropylmethyl-(5-{4-[2-(3,4-difluoro-phenyl)-ethyl]-piperazin-1-yl}-[1,2,4]thiadiazol-3-yl)-amine

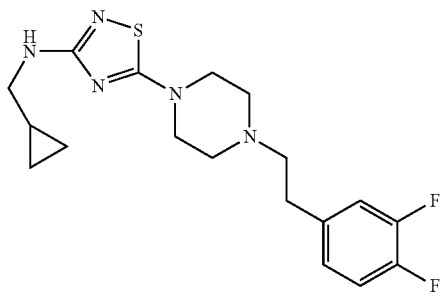 [SMILES: Fc1ccc(CCN2CCN(c3nc(NCC4CC4)ns3)CC2)cc1F]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(3,4-difluoro-phenyl)-ethyl]-piperazine and cyclopropylmethanamine. MS (m/e): 380.3 (MH+).

Example 16

(5-{4-[2-(3,4-Difluoro-phenyl)-ethyl]-piperazin-1-yl}-[1,2,4]thiadiazol-3-yl)-(tetrahydro-pyran-4-yl)-amine

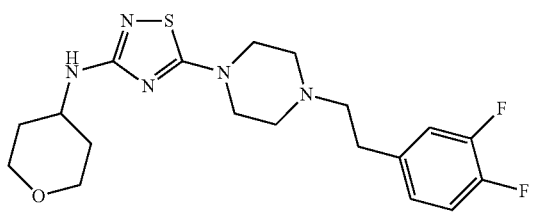 [SMILES: Fc1ccc(CCN2CCN(c3nc(NC4CCOCC4)ns3)CC2)cc1F]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(3,4-difluoro-phenyl)-ethyl]-piperazine and tetrahydro-2H-pyran-4-amine. MS (m/e): 410.3 (MH+).

Example 17

Cyclohexyl-(5-{4-[2-(3,4-difluoro-phenyl)-ethyl]-piperazin-1-yl}-[1,2,4]thiadiazol-3-yl)-amine In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]thiadiazol-5-yl)-4-[2-(3,4-difluoro-phenyl)-ethyl]-piperazine and cyclohexanamine. MS (m/e): 408.4 (MH+).

Example 18

1-[2-(3,4-Difluoro-phenyl)-ethyl]-4-(3-piperidin-1-yl-[1,2,4]thiadiazol-5-yl)-piperazine

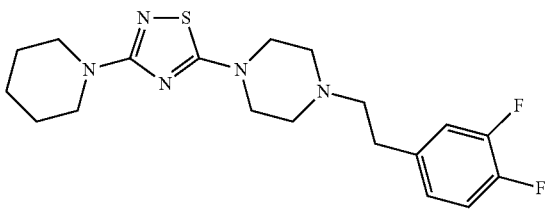 [SMILES: Fc1ccc(CCN2CCN(c3nc(N4CCCCC4)ns3)CC2)cc1F]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4]

thiadiazol-5-yl)-4-[2-(3,4-difluoro-phenyl)-ethyl]-piperazine and piperidine. MS (m/e): 394.2 (MH⁺).

Example 19

(5-{4-[2-(3,4-Difluoro-phenyl)-ethyl]-piperazin-1-yl}-[1,2,4]thiadiazol-3-yl)-(4-trifluoromethyl-cyclohexyl)-amine

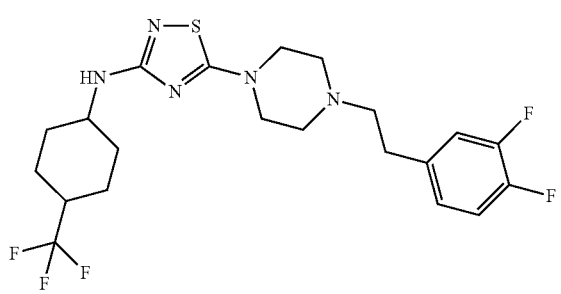 [SMILES: Fc1ccc(CCN2CCN(c3nc(NC4CCC(C(F)(F)F)CC4)ns3)CC2)cc1F]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4] thiadiazol-5-yl)-4-[2-(3,4-difluoro-phenyl)-ethyl]-piperazine and 4-(trifluoromethyl)cyclohexanamine. MS (m/e): 476.2 (MH⁺).

Example 20

Butyl-(5-{4-[2-(3,4-difluoro-phenyl)-ethyl]-piperazin-1-yl}-[1,2,4]thiadiazol-3-yl)-ethyl-amine

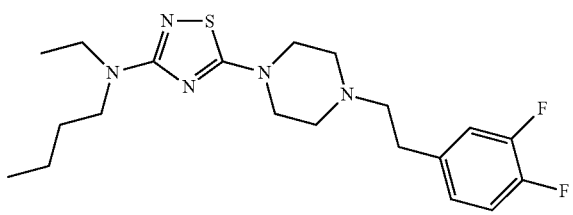 [SMILES: CCCCN(CC)c1nsc(N2CCN(CCc3ccc(F)c(F)c3)CC2)n1]

In analogy to the procedure described for the synthesis of 1-[3-(4,4-difluoro-piperidin-1-yl)-[1,2,4]thiadiazol-5-yl]-4-[2-(4-methoxy-phenyl)-ethyl]-piperazine (example 1, step b) the title compound was prepared from 1-(3-bromo-[1,2,4] thiadiazol-5-yl)-4-[2-(3,4-difluoro-phenyl)-ethyl]-piperazine and N-ethylbutan-1-amine. MS (m/e): 410.3 (MH⁺).

Example 21

1-(3-Cyclohexyl-[1,2,4]thiadiazol-5-yl)-4-[2-(4-methoxy-phenyl)-ethyl]-piperazine

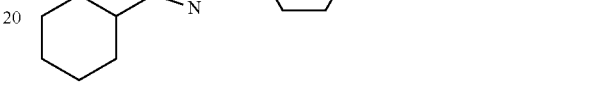

a) 5-Chloro-3-cyclohexyl-[1,2,4]thiadiazole

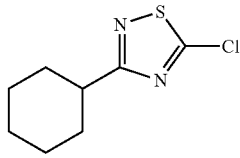 [SMILES: Clc1nc(C2CCCCC2)ns1]

Cyclohexanecarboximidamide (100 mg, 792 μmol) and DIPEA (512 mg, 3.96 mmol) in 10 mL DCM at 0-5° C. were treated with perchloromethyl mercaptan (147 mg, 792 μmol) in 5 mL DCM and stirred for 1 hr at 0-5° C. The mixture was concentrated in vacuo to give a brown solid which was used with out further purification in the subsequent step.

b) 1-(3-Cyclohexyl-[1,2,4]thiadiazol-5-yl)-4-[2-(4-methoxy-phenyl)-ethyl]-piperazine A mixture of 5-chloro-3-cyclohexyl-1,2,4-thiadiazole (32.0 mg, 158 μmol), 1-(4-methoxyphenethyl)piperazine dihydrochloride (51.0 mg, 174 μmol) and DIPEA in EtOH was heated for 30 min at an oil bath temperature of 90° C. The mixture was subjected to purification by preparative HPLC on reversed phase eluting with a gradient formed from acetonitrile, water and NEt₃ to yield after evaporation of the product containing fractions 13.7 mg (22%) of the title compound as light brown solid. MS (m/e): 387.3 (MH⁺).

Example 22

1-(3-Cyclohexyl-[1,2,4]thiadiazol-5-yl)-4-[2-(3-methoxy-phenyl)-ethyl]-piperazine

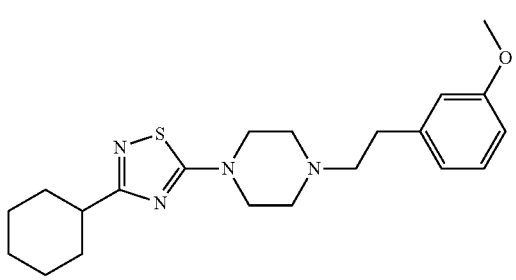 [SMILES: COc1cccc(CCN2CCN(c3nc(C4CCCCC4)ns3)CC2)c1]

In analogy to the procedure described for the synthesis of 1-(3-cyclohexyl-[1,2,4]thiadiazol-5-yl)-4-[2-(4-methoxy-phenyl)-ethyl]-piperazine (example 21, step b) the title compound was prepared from 5-chloro-3-cyclohexyl-[1,2,4]thiadiazole and 1-(3-methoxyphenethyl)piperazine dihydrochloride as light brown solid. MS (m/e): 387.3 (MH⁺).

Example 23

1-(3-Butyl-[1,2,4]thiadiazol-5-yl)-4-[2-(4-methoxy-phenyl)-ethyl]-piperazine

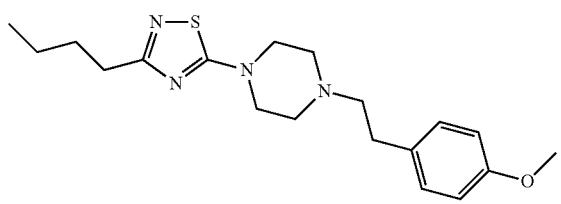 [SMILES: CCCCc1nsc(N2CCN(CCc3ccc(OC)cc3)CC2)n1]

In analogy to the procedure described for the synthesis of 1-(3-cyclohexyl-[1,2,4]thiadiazol-5-yl)-4-[2-(4-methoxy-phenyl)-ethyl]-piperazine (example 21, step b) the title compound was prepared from 3-butyl-5-chloro-[1,2,4]thiadiazole and 1-(4-methoxyphenethyl)piperazine dihydrochloride. MS (m/e): 361.3 (MH⁺).

Example 24

1-(3-Cyclopropyl-[1,2,4]thiadiazol-5-yl)-4-[2-(4-methoxy-phenyl)-ethyl]-piperazine

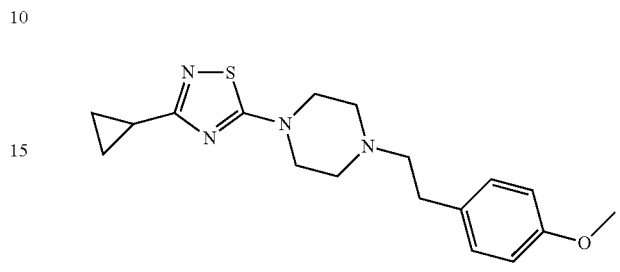

In analogy to the procedure described for the synthesis of 1-(3-cyclohexyl-[1,2,4]thiadiazol-5-yl)-4-[2-(4-methoxy-phenyl)-ethyl]-piperazine (example 21, step b) the title compound was prepared from 5-chloro-3-cyclopropyl-[1,2,4]thiadiazole and 1-(4-methoxyphenethyl)piperazine dihydrochloride. MS (m/e): 345.2 (MH⁺).

Example 25

1-(3-Butyl-[1,2,4]thiadiazol-5-yl)-4-[2-(3-methoxy-phenyl)-ethyl]-piperazine

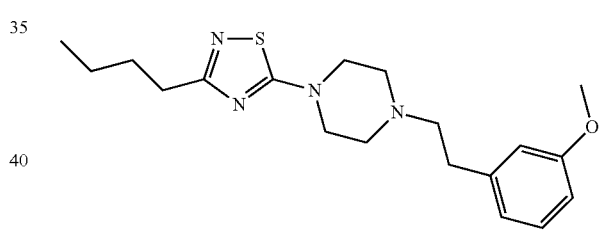

In analogy to the procedure described for the synthesis of 1-(3-cyclohexyl-[1,2,4]thiadiazol-5-yl)-4-[2-(4-methoxy-phenyl)-ethyl]-piperazine (example 21, step b) the title compound was prepared from 3-butyl-5-chloro-[1,2,4]thiadiazole and 1-(3-methoxyphenethyl)piperazine dihydrochloride. MS (m/e): 361.3 (MH⁺).

Example 26

1-(3-Cyclopropyl-[1,2,4]thiadiazol-5-yl)-4-[2-(3-methoxy-phenyl)-ethyl]-piperazine

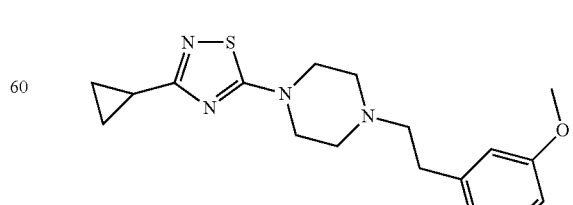

In analogy to the procedure described for the synthesis of 1-(3-cyclohexyl-[1,2,4]thiadiazol-5-yl)-4-[2-(4-methoxyphenyl)-ethyl]-piperazine (example 21, step b) the title compound was prepared from 5-chloro-3-cyclopropyl-[1,2,4]thiadiazole and 1-(3-methoxyphenethyl)piperazine dihydrochloride. MS (m/e): 345.2 (MH$^+$).

Example 27

1-[2-(4-Fluoro-phenyl)-ethyl]-4-[3-(tetrahydro-pyran-4-yl)-[1,2,4]thiadiazol-5-yl]-piperazine

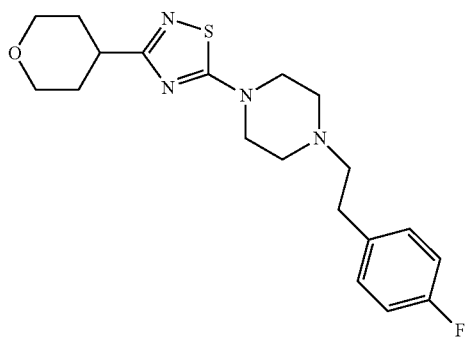 [SMILES: Fc1ccc(CCN2CCN(c3nc(C4CCOCC4)ns3)CC2)cc1]

In analogy to the procedure described for the synthesis of 1-(3-cyclohexyl-[1,2,4]thiadiazol-5-yl)-4-[2-(4-methoxyphenyl)-ethyl]-piperazine (example 21, step b) the title compound was prepared from 5-chloro-3-(tetrahydro-pyran-4-yl)-[1,2,4]thiadiazole and 1-(4-fluorophenethyl)piperazine dihydrochloride. MS (m/e): 377.3 (MH$^+$).

Example 28

1-[2-(4-Methoxy-phenyl)-ethyl]-4-[3-(tetrahydro-pyran-4-yl)-[1,2,4]thiadiazol-5-yl]-piperazine

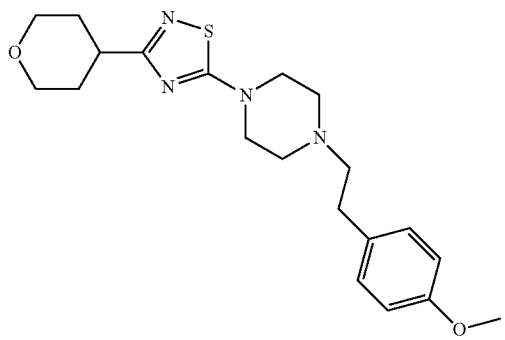 [SMILES: COc1ccc(CCN2CCN(c3nc(C4CCOCC4)ns3)CC2)cc1]

In analogy to the procedure described for the synthesis of 1-(3-cyclohexyl-[1,2,4]thiadiazol-5-yl)-4-[2-(4-methoxyphenyl)-ethyl]-piperazine (example 21, step b) the title compound was prepared from 5-chloro-3-(tetrahydro-pyran-4-yl)-[1,2,4]thiadiazole and 1-(4-methoxyphenethyl) piperazine dihydrochloride. MS (m/e): 389.3 (MH$^+$).

Example 29

1-[2-(2-Methoxy-pyridin-4-yl)-ethyl]-4-[3-(tetrahydro-pyran-4-yl)-[1,2,4]thiadiazol-5-yl]-piperazine

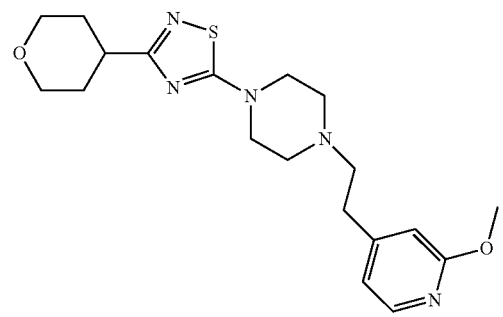 [SMILES: COc1cc(CCN2CCN(c3nc(C4CCOCC4)ns3)CC2)ccn1]

In analogy to the procedure described for the synthesis of 1-(3-cyclohexyl-[1,2,4]thiadiazol-5-yl)-4-[2-(4-methoxyphenyl)-ethyl]-piperazine (example 21, step b) the title compound was prepared from 5-chloro-3-(tetrahydro-pyran-4-yl)-[1,2,4]thiadiazole and 1-(2-(2-methoxypyridin-4-yl) ethyl)piperazine trihydrochloride. MS (m/e): 390.3 (MH$^+$).

Example 30

1-(2-Methyl-benzyl)-4-[3-(tetrahydro-pyran-4-yl)-[1,2,4]thiadiazol-5-yl]-piperazine

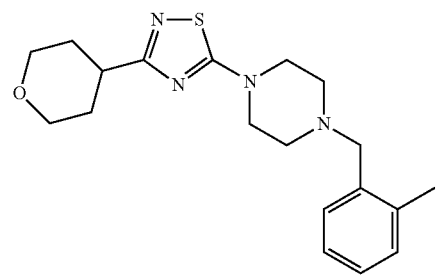 [SMILES: Cc1ccccc1CN1CCN(c2nc(C3CCOCC3)ns2)CC1]

a) 1-[3-(Tetrahydro-pyran-4-yl)-[1,2,4]thiadiazol-5-yl]-piperazine

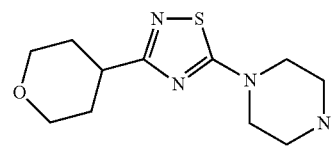 [SMILES: C1CN(c2nc(C3CCOCC3)ns2)CCN1]

A mixture of 5-chloro-3-(tetrahydro-2H-pyran-4-yl)-1,2,4-thiadiazole (2.1 g, 10.3 mmol) and piperazine (8.84 g, 103 mmol) in EtOH (50 mL) was stirred at room temperature and concentrated in vacuo. The residue was purified by silica column chromatography eluting with a gradient formed from DCM, methanol and NH$_3$ to yield, after evaporation of the product containing fractions 2.48 g (95%) of the title compound as light brown solid. MS (m/e): 255.1 (MH+).

b) 1-(2-Methyl-benzyl)-4-[3-(tetrahydro-pyran-4-yl)-[1,2,4]thiadiazol-5-yl]-piperazine A mixture of 5-(piperazin-1-yl)-3-(tetrahydro-2H-pyran-4-yl)-1,2,4-thiadiazole (19.1 mg, 75.0 μmol), 1-(chloromethyl)-2-methylbenzene (31.6 mg, 225 μmol) and DIPEA (96.9 mg, 131 μL, 750 μmol) in N-methyl-2-pyrrolidinone (1 mL) was heated under microwave irradiation for 10 min at 180° C. The resulting reaction solution was purified by preparative HPLC on reversed phase eluting with a gradient formed from acetonitrile, water and NEt₃ to yield, after evaporation of the product containing fractions 13 mg (48%) of the title compound. MS (m/e): 359.2 (MH+).

Example 31

1-[2-(3,4-Difluoro-phenyl)-ethyl]-4-[3-(tetrahydro-pyran-4-yl)-[1,2,4]thiadiazol-5-yl]-piperazine

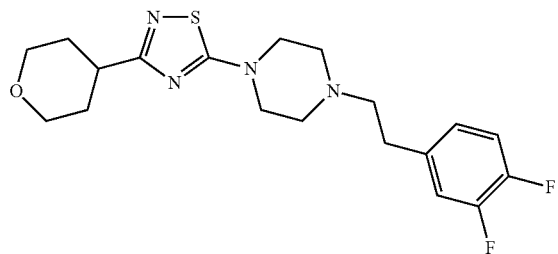 [SMILES: Fc1ccc(CCN2CCN(c3nc(C4CCOCC4)ns3)CC2)cc1F]

In analogy to the procedure described for the synthesis of 1-(2-methyl-benzyl)-4-[3-(tetrahydro-pyran-4-yl)-[1,2,4]thiadiazol-5-yl]-piperazine (example 30, step b) the title compound was prepared from 1-[3-(tetrahydro-pyran-4-yl)-[1,2,4]thiadiazol-5-yl]-piperazine and 4-(2-bromoethyl)-1,2-difluorobenzene. MS (m/e): 395.2 (MH+).

Example 37

5-(4-(4-methoxyphenethyl)piperazin-1-yl)-3-(trifluoromethyl)-1,2,4-thiadiazole

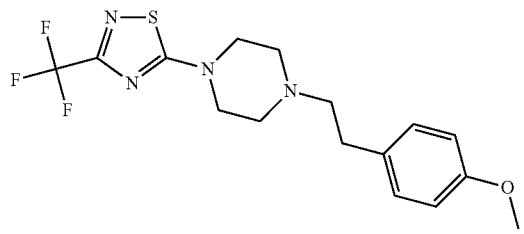 [SMILES: COc1ccc(CCN2CCN(c3nc(C(F)(F)F)ns3)CC2)cc1]

In analogy to the procedure described for the synthesis of 1-(2-methyl-benzyl)-4-[3-(tetrahydro-pyran-4-yl)-[1,2,4]thiadiazol-5-yl]-piperazine (example 30, step b) the title compound is prepared from 5-(piperazin-1-yl)-3-(trifluoromethyl)-1,2,4-thiadiazole and 1-(2-bromoethyl)-4-methoxybenzene.

Construction of a TAU Gene Over-expressing Cell Line

A TAU expression plasmid was constructed by sub-cloning the cDNA encoding for human TAU-P301L protein, wherein proline at position 301 is substituted by a leucine residue, into mammalian expression vector pcDNA3.1 resulting in the plasmid pcDNA3.1-TAUP301L. Plasmids pcDNA3.1 and pcDNA3.1-TAU P301L were transfected into human neuroblastoma cells (BE-M17; ATCC No. CRL2267™) using lipofectamine reagent and subsequently, independent clonal cell lines with the plasmids stably integrated into the genome were selected by antibiotic resistance selection (Geneticin (G418)), resulting in cell lines M17.pcDNA3 and M17_3TAUP301L. Expression of the TAUP301L gene in the M17_3TAUP301L cells was confirmed by Western blot analysis.

Use of TAU Expressing Cells as a Model of Neuronal Degeneration

The expression of TAU P301L in M17_3TAU(P301L) cells was found to confer increased toxicity relative to control cells expressing no TAU after 7 days of cell differentiation using retinoic acid (RA). Differentiation of the cells with RA leads to phosphorylation and subsequent aggregation of TAU, inducing a tauopathy in these cells. Cytotoxicity of cells was measured by quantification of lactate dehydrogenase (LDH) levels. In dead cells LDH is leaked out of the cells into the medium due to a loss of plasma-membrane integrity.

Briefly, 3 days preceeding the experiment pre-cultures of M17.pcDNA3 and M17_3TAU(P301L) cells were prepared, starting from a stock culture, at a density of 50.000-100.000 cells/cm2 in detection medium (Optimem Reduced Serum without phenol red (Gibco, Cat. 31985-047) supplemented with 1% fetal calf serum (FCS), 1 mM sodium pyruvate, 1× non-essential amino acids (NEAA), 500 μg/ml G418 and 0.5× antibiotic/antimycotic (ABAM)). At the day of the experiment these precultures were diluted to ~0.1.106 cells/ml in detection medium without FCS and 60 μL of this suspension is dispensed per well into a 96-well microtiter plate. After 3 hours of incubation at 37° C./5% CO2 an equal volume of detection medium containing 2.5 μM RA was added and subsequently incubated for 7 days at 37° C./5% CO₂. After 7 days, LDH activity was determined using the Promega Cytotox 96 Non-Radioactive cytotoxicity assay (Cat. G1780), according the manufacturer's instructions. Cytotoxicity is measured as the ratio of LDH increase in the supernatant divided by the LDH increase in the total cell suspension (sum of the LDH measured in cells and supernatant). FIG. 1 shows toxicity after 7 days of differentiation with retinoic acid in M17_3TAU(P301L) cells compared to M17.pcDNA3 cells. Toxicity is clearly higher in the M17_3TAU(P301L) cells demonstrating that it is specifically provoked by the presence of the mutant TAU P301 protein.

Use of the Neuroblastoma Tauopathy Model to Screen Compounds

The M17_3TAU(P301L) cell line makes it possible to assess the ability of novel compounds to inhibit TAU-induced cytotoxicity. Active inhibitors of Tauopathy in these cells were found to inhibit cytotoxicity or LDH increase in the medium of M17_3TAU(P301L) cells treated as described in Example above. Compounds were tested for their ability to hamper TAU-induced toxicity at different concentrations, ranging from low non-effective concentrations to high potent concentrations. Afterwards, the dose-dependent inhibition curve was used to calculate their $EC_{50}$ (Table III).

Although the pharmacological properties of the compounds disclosed in this invention vary with structural change, active compounds most particularly possess $EC_{50}$ in a cell-based assay in a range from about 0.0005 to 1.0 μM.

The tested compounds show a EC$_{50}$ value (μM) as shown in table III.

TABLE III

| Example | EC$_{50}$ (μM) |
|---|---|
| 1 | 0.0006 |
| 2 | 0.0536 |
| 3 | 0.0088 |
| 4 | 0.0846 |
| 5 | 0.047 |
| 6 | 0.0641 |
| 7 | 0.0172 |
| 8 | 0.0522 |
| 9 | 0.0094 |
| 10 | 0.0121 |
| 11 | 0.0114 |
| 12 | 0.0333 |
| 13 | 0.0153 |
| 14 | 0.1757 |
| 15 | 0.0384 |
| 16 | 0.0345 |
| 17 | 0.0038 |
| 18 | 0.0464 |
| 19 | 0.3403 |
| 20 | 0.7088 |
| 21 | 0.0022 |
| 22 | 0.003 |
| 23 | 0.0005 |
| 24 | 0.0445 |
| 25 | 0.0022 |
| 26 | 0.4102 |
| 27 | 0.3088 |
| 28 | 0.0333 |
| 29 | 0.2027 |
| 30 | 0.4135 |
| 31 | 0.3085 |

The compounds of formula IA or I and the pharmaceutically acceptable salts of the compounds of formula IA or I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula IA or I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula IA or I or a pharmaceutically acceptable salt thereof and a therapeutically inert carrier are also an object of the present invention, as is a process for their production, which comprises bringing one or more compounds of formula IA or I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of Alzheimer's disease, Pick's disease, corticobasal degeneration, progressive supranuclear palsy, frontotemporal dementia and parkinsonism (linked to chromosome 17, FTDP-17).

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:

1. A compound of formula IA or a pharmaceutically active salt thereof, to a stereoisomeric form, including an individual diastereoisomer or enantiomer of the compound of formula (IA) as well as to a racemic or non-racemic mixture thereof;

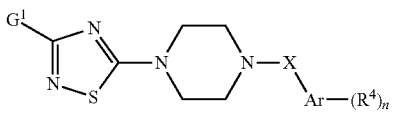

wherein
- G¹ is lower alkyl; lower alkyl substituted by one or more halogens; cycloalkyl; tetrahydropyran-4-yl; phenethyl; phenethyl substituted by one or more halogens; phenoxymethyl; phenoxymethyl substituted by one or more halogens; benzyloxy-ethyl; benzyloxy-ethyl substituted by one or more halogens; or is —NR²R³;
- R² is hydrogen or lower alkyl;
- R³ is lower alkyl, tetrahydropyran-4-yl, —CH₂-cycloalkyl or cycloalkyl optionally substituted by lower alkyl substituted by one or more halogens; or R² and R³ form together with the N-atom to which they are attached a heterocycloalkyl group with 4 or 5 carbon atoms, which is optionally substituted by one or more substituents selected from halogen or lower alkyl substituted by one or more halogens;
- X is —CH₂— or —(CH₂)₂—;
- Ar is phenyl or pyridinyl;
- R⁴ is halogen; lower alkyl; lower alkyl substituted by one or more halogens; or lower alkoxy;
- n is 1 or 2;

with the proviso that said compound is not:
5-(4-(3-fuorobenzyl)piperazin-1-yl)-3-methyl-1,2,4-thiadiazole and
3-isopropyl-5-(4-(3-(trifluoromethyl)benzyl)piperazin-1-yl)-1,2,4-thiadiazole.

2. A compound of formula IA according to claim 1, wherein X is —(CH₂)₂—.

3. A compound of formula IA according to claim 2, which compounds are
1-[3-(4,4-Difluoro-piperidin-1-yl)-[1,2,4]thiadiazol-5-yl]-4-[2-(4-methoxy-phenyl)-ethyl]-piperazine
1-[2-(4-Chloro-phenyl)-ethyl]-4-[3-(4,4-difluoro-piperidin-1-yl)-[1,2,4]thiadiazol-5-yl]-piperazine
1-[2-(4-Chloro-phenyl)-ethyl]-4-[3-(3,3-difluoro-pyrrolidin-1-yl)-[1,2,4]thiadiazol-5-yl]-piperazine
1-[2-(4-Chloro-phenyl)-ethyl]-4-[3-(4-fluoro-piperidin-1-yl)-[1,2,4]thiadiazol-5-yl]-piperazine
1-[2-(4-Chloro-phenyl)-ethyl]-4-[3-(4-trifluoromethyl-piperidin-1-yl)-[1,2,4]thiadiazol-5-yl]-piperazine
1-[2-(4-Chloro-phenyl)-ethyl]-4-(3-piperidin-1-yl-[1,2,4]thiadiazol-5-yl)-piperazine
(5-{4-[2-(4-Chloro-phenyl)-ethyl]-piperazin-1-yl}-[1,2,4]thiadiazol-3-yl)-cyclopropylmethyl-amine
(5-{4-[2-(4-Chloro-phenyl)-ethyl]-piperazin-1-yl}-[1,2,4]thiadiazol-3-yl)-(tetrahydro-pyran-4-yl)-amine
(5-{4-[2-(4-Chloro-phenyl)-ethyl]-piperazin-1-yl}-[1,2,4]thiadiazol-3-yl)-cyclohexyl-amine
1-[2-(3,4-Difluoro-phenyl)-ethyl]-4-[3-(4,4-difluoro-piperidin-1-yl)-[1,2,4]thiadiazol-5-yl ]-piperazine
1-[2-(3,4-Difluoro-phenyl)-ethyl]-4-[3-(3,3-difluoro-pyrrolidin-1-yl)-[1,2,4]thiadiazol-5-y1]-piperazine
1-[2-(3,4-Difluoro-phenyl)-ethyl]-4-[3-(4-fluoro-piperidin-1-yl)-[1,2,4]thiadiazol-5-yl]-piperazine
1-[2-(3,4-Difluoro-phenyl)-ethyl]-4-[3-(4-trifluoromethyl-piperidin-1-yl)-[1,2,4]thiadiazol-5-yl]-piperazine
1-[2-(3,4-Difluoro-phenyl)-ethyl]-4-(3-pyrrolidin-1-yl-[1,2,4]thiadiazol-5-yl)-piperazine
Cyclopropylmethyl-(5-{4-[2-(3,4-difluoro-phenyl)-ethyl]-piperazin-1-yl}-[1,2,4]thiadiazol-3-yl)-amine
(5-{4-[2-(3,4-Difluoro-phenyl)-ethyl]-piperazin-1-yl}-[1,2,4]thiadiazol-3-yl)-(tetrahydro-pyran-4-yl)-amine
Cyclohexyl-(5-{4-[2-(3,4-difluoro-phenyl)-ethyl]-piperazin-1-yl}-[1,2,4]thiadiazol-3-yl)-amine
1-[2-(3,4-Difluoro-phenyl)-ethyl]-4-(3-piperidin-1-yl-[1,2,4]thiadiazol-5-yl)-piperazine
(5-{4-[2-(3,4-Difluoro-phenyl)-ethyl]-piperazin-1-yl}-[1,2,4]thiadiazol-3-yl)-(4-trifluoromethyl-cyclohexyl)-amine
Butyl-(5-{4-[2-(3,4-difluoro-phenyl)-ethyl]-piperazin-1-yl}-[1,2,4]thiadiazol-3-yl)-ethyl-amine
1-(3-Cyclohexyl-[1,2,4]thiadiazol-5-yl)-4-[2-(4-methoxy-phenyl)-ethyl]-piperazine
1-(3-Cyclohexyl-[1,2,4]thiadiazol-5-yl)-4-[2-(3-methoxy-phenyl)-ethyl]-piperazine
1-(3-Butyl-[1,2,4]thiadiazol-5-yl)-4-[2-(4-methoxy-phenyl)-ethyl]-piperazine
1-(3-Cyclopropyl-[1,2,4]thiadiazol-5-yl)-4-[2-(4-methoxyl-phenyl)-ethyl]-piperazine
1-(3-Butyl-[1,2,4]thiadiazol-5-yl)-4-[2-(3-methoxy-phenyl)-ethyl]-piperazine
1-(3-Cyclopropyl-[1,2,4]thiadiazol-5-yl)-4-[2-(3-methoxy-phenyl)-ethyl]-piperazine
1-[2-(4-Fluoro-phenyl)-ethyl]-4-[3-(tetrahydro-pyran-4-yl)-[1,2,4]thiadiazol-5-yl]-piperazine
1-[2-(4-Methoxyl-phenyl)-ethyl]-4-[3-(tetrahydro-pyran-4-yl)-[1,2,4]thiadiazol-5-yl]-piperazine
1-[2-(2-Methoxy-pyridin-4-yl)-ethyl]-4-[3-(tetrahydro-pyran-4-yl)-[1,2,4]thiadiazol-5-yl]-piperazine
1-[2-(3,4-Difluoro-phenyl)-ethyl]-4-[3-(tetrahydro-pyran-4-yl)-[1,2,4]thiadiazol-5-yl]-piperazine
3-((3-chlorophenoxy)methyl)-5-(4-(3-methoxyphenethyl)piperazin-yl)-1,2,4-thiadiazole
3-(2-(benzyloxy)ethyl)-5-(4-(3-methoxyphenethyl)piperazin-1-yl)-1,2,4-thiadiazole
3-((4-fluorophenoxy)methyl)-5-(4-(3-methoxyphenethyl)piperazin-1-yl)-1,2,4-thiadiazole
3-((4-fluorophenoxy)methyl)-5-(4-(4-methoxyphenethyl)piperazin-1-yl)-1,2,4-thiadiazole or
5-(4-(4-methoxyphenethyl)piperazin-1-yl)-3-(trifluoromethyl)-1,2,4-thiadiazole.

4. A compound of formula IA according to claim 1, wherein G¹ is lower alkyl; cycloalkyl; tetrahydropyran-4-yl;-phenoxymethyl substituted by one or more halogens; benzyloxy-ethyl; or benzyloxy-ethyl substituted by one or more halogens.

5. A compound of formula IA according to claim 4, wherein the compounds are
1-(3-Cyclohexyl-[1,2,4]thiadiazol-5-yl)-4-[2-(4-methoxy-phenyl)-ethyl]-piperazine
1-(3-Cyclohexyl-[1,2,4]thiadiazol-5-yl)-4-[2-(3-methoxy-phenyl)-ethyl]-piperazine
1-(3-Butyl-[1,2,4]thiadiazol-5-yl)-4-[2-(4-methoxy-phenyl)-ethyl]-piperazine
1-(3-Cyclopropyl-[1,2,4]thiadiazol-5-yl)-4-[2-(4-methoxy-phenyl)-ethyl]-piperazine
1-(3-Butyl-[1,2,4]thiadiazol-5-yl)-4-[2-(3-methoxy-phenyl)-ethyl]-piperazine
1-(3-Cyclopropyl-[1,2,4]thiadiazol-5-yl)-4-[2-(3-methoxy-phenyl)-ethyl]-piperazine
1-[2-(4-Fluoro-phenyl)-ethyl[-4-]3-(tetrahydro-pyran-4-yl)-[1,2,4]thiadiazol-5-yl]-piperazine
1-[2-(4-Methoxy-phenyl)-ethyl[-4-]3-(tetrahydro-pyran-4-yl)-[1,2,4]thiadiazol-5-yl]-piperazine 1-[2-(2-Methoxy-pyridin-4-yl)-ethyl]-4-[3-(tetrahydro-pyran-4-yl)-[1,2,4]thiadiazol-5-yl]-piperazine
1-[2-(3,4-Difluoro-phenyl)-ethyl]-4-[3-(tetrahydro-pyran-4-yl)-[1,2,4]thiadiazol-5-yl]-piperazine or
3-((3-chlorophenoxy)methyl)-5-(4-(3-methoxyphenethyl)piperazin-1-yl)-1,2,4-thiadiazole
3-(2-(benzyloxy)ethyl)-5-(4-(3-methoxyphenethyl)piperazin-1-yl)-1,2,4-thiadiazole
3-((4-fluorophenoxy)methyl)-5-(4-(3-methoxyphenethyl)piperazin-1-yl)-1,2,4-thiadiazole or
3-((4-fluorophenoxy)methyl)-5-(4-(4-methoxyphenethyl)piperazin-1-yl)-1,2,4-thiadiazole.

6. A compound of formula IA according to claim 1, wherein $G^1$ is —$NR^2R^3$.

7. A compound of formula IA according to claim 6, wherein $R^2$ is hydrogen and $R^3$ is lower alkyl, tetrahydropyran-4-yl, —$CH_2$-cycloalkyl, or cycloalkyl optionally substituted by lower alkyl substituted by one or more halogens.

8. A compound of formula IA according to claim 7, wherein the compounds are
(5-{4-[2-(4-Chloro-phenyl)-ethyl]-piperazin-1-yl}-[1,2,4]thiadiazol-3-yl)-cyclopropylmethyl-amine
(5-{4-[2-(4-Chloro-phenyl)-ethyl]-piperazin-1-yl}-[1,2,4]thiadiazol-3-yl)-(tetrahydro-pyran-4-yl)-amine
(5-{4-[2-(4-Chloro-phenyl)-ethyl]-piperazin-1-yl}-[1,2,4]thiadiazol-3-yl)-cyclohexyl-amine
Cyclopropylmethyl-(5-{4-[2-(3,4-difluoro-phenyl)-ethyl]-piperazin-1-yl}-[1,2,4]thiadiazol-3-yl)-amine
(5-{4-[2-(3,4-Difluoro-phenyl)-ethyl]-piperazin-1-yl}-[1,2,4]thiadiazol-3-yl)-(tetrahydro-pyran-4-yl)-amine
Cyclohexyl-(5-{4-[2-(3,4-difluoro-phenyl)-ethyl]-piperazin-1-yl}-[1,2,4]thiadiazol-3-yl)-amine or
(5-{4-[2-(3,4-Difluoro-phenyl)-ethyl]-piperazin-1-yl}-[1,2,4]thiadiazol-3-yl)-(4-trifluoromethyl-cyclohexyl)-amine.

9. A compound of formula IA according to claim 6, wherein $R^2$ and $R^3$ form together with the N-atom to which they are attached a heterocycloalkyl group with 4 or 5 carbon atoms, which is optionally substituted by one or more substituents selected from halogen or lower alkyl substituted by one or more halogens.

10. A compound of formula IA according to claim 9, which compounds are
1-[3-(4,4-Difluoro-piperidin-1-yl)-[1,2,4]thiadiazol-5-yl]-4-[2-(4-methoxy-phenyl)-ethyl]-piperazine
1-[2-(4-Chloro-phenyl)-ethyl]-4-[3-(4,4-difluoro-piperidin-1-yl)-[1,2,4]thiadiazol-5-yl]-piperazine
1-[2-(4-Chloro-phenyl)-ethyl]-4-[3-(3,3-difluoro-pyrrolidin-1-yl)-[1,2,4]thiadiazol-5-yl]-piperazine
1-[2-(4-Chloro-phenyl)-ethyl]-4-[3-(4-fluoro-piperidin-1-yl)-[1,2,4]thiadiazol-5-yl]-piperazine
1-[2-(4-Chloro-phenyl)-ethyl]-4-[3-(4-trifluoromethyl-piperidin-1-yl)-[1,2,4]thiadiazol-5-yl ]-piperazine
1-[2-(4-Chloro-phenyl)-ethyl]-4-(3-piperidin-1-yl-[1,2,4]thiadiazol-5-yl)-piperazine
1-[2-(3,4-Difluoro-phenyl)-ethyl]-4-[3-(4,4-difluoro-piperidin-1-yl)-[1,2,4]thiadiazol-5-yl ]-piperazine
1-[2-(3,4-Difluoro-phenyl)-ethyl]-4-[3-(3,3-difluoro-pyrrolidin-1-yl)-[1,2,4]thiadiazol-5-yl ]-piperazine
1-[2-(3,4-Difluoro-phenyl)-ethyl]-4-[3-(4-fluoro-piperidin-1-yl)-[1,2,4]thiadiazol-5-yl]-piperazine
1-[2-(3,4-Difluoro-phenyl)-ethyl]-4-[3-(4-trifluoromethyl-piperidin-1-yl)-[1,2,4]thiadiazol-5-yl]-piperazine
1-[2-(3,4-Difluoro-phenyl)-ethyl]-4-(3-pyrrolidin-1-yl-[1,2,4]thiadiazol-5-yl)-piperazine
1-[2-(3,4-Difluoro-phenyl)-ethyl]-4-(3-piperidin-1-yl-[1,2,4]thiadiazol-5-yl)-piperazine.

11. A process for preparation of compounds of formula IA according to claim 1, which process comprises
coupling a compound of formula

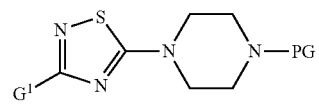

with a compound of formula

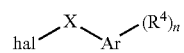

to give a compound of formula

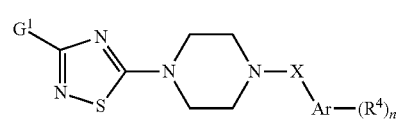

wherein the definitions are as described in claim 1, wherein PG is hydrogen or a protecting group, and hal is a halogen or if desired, converting the compounds obtained into pharmaceutically acceptable acid addition salts, wherein when PG is a protecting group, the compound of formula IV is deprotected under suitable conditions prior to coupling.

12. A compound according to claim 1, when manufactured according to a process of
coupling a compound of formula

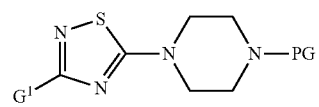

with a compound of formula

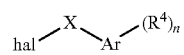

to give a compound of formula

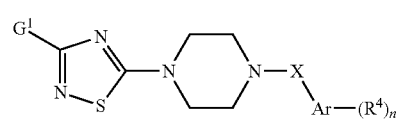

wherein the definitions are as described in claim 1, wherein PG is hydrogen or a protecting group, and hal is a halogen or if desired, converting the compounds obtained into pharmaceutically acceptable acid addition salts, wherein when PG is a protecting group, the compound of formula IV is deprotected under suitable conditions prior to coupling.

13. A pharmaceutical composition containing one or more compounds as claimed in claim 1 and pharmaceutically acceptable excipients.

14. A compound selected from the group consisting of
- 1-[3-(4,4-Difluoro-piperidin-1-yl)-[1,2,4]thiadiazol-5-yl]-4-[2-(4-methoxy-phenyl)-ethyl]-piperazine
- 1-[2-(4-Chloro-phenyl)-ethyl]-4-[3-(4,4-difluoro-piperidin-1-yl)-[1,2,4]thiadiazol-5-yl]-piperazine
- 1-[2-(4-Chloro-phenyl)-ethyl]-4-[3-(3,3-difluoro-pyrrolidin-1-yl)-[1,2,4]thiadiazol-5-yl]-piperazine
- 1-[2-(4-Chloro-phenyl)-ethyl]-4-[3-(4-fluoro-piperidin-1-yl)-[1,2,4]thiadiazol-5-yl]-piperazine
- 1-[2-(4-Chloro-phenyl)-ethyl]-4-[3-(4-trifluoromethyl-piperidin-1-yl)-[1,2,4]thiadiazol-5-yl ]-piperazine
- 1-[2-(4-Chloro-phenyl)-ethyl]-4-(3-piperidin-1-yl-[1,2,4]thiadiazol-5-yl)-piperazine
- (5-{4-[2-(4-Chloro-phenyl)-ethyl]-piperazin-1-yl}-[1,2,4]thiadiazol-3-yl)-cyclopropylmethyl-amine
- (5-{4-[2-(4-Chloro-phenyl)-ethyl]-piperazin-1-yl}-[1,2,4]thiadiazol-3-yl)-(tetrahydro-pyran-4-yl)-amine
- (5-{4-[2-(4-Chloro-phenyl)-ethyl]-piperazin-1-yl}-[1,2,4]thiadiazol-3-yl)-cyclohexyl-amine
- 1-[2-(3,4-Difluoro-phenyl)-ethyl]-4-[3-(4,4-difluoro-piperidin-1-yl)-[1,2,4]thiadiazol-5-yl ]-piperazine
- 1-[2-(3,4-Difluoro-phenyl)-ethyl]-4-[3-(3,3-difluoro-pyrrolidin-1-yl)-[1,2,4]thiadiazol-5-yl ]-piperazine
- 1-[2-(3,4-Difluoro-phenyl)-ethyl]-4-[3-(4-fluoro-piperidin-1-yl)-[1,2,4]thiadiazol-5-yl]-piperazine
- 1-[2-(3,4-Difluoro-phenyl)-ethyl]-4-[3-(4-trifluoromethyl-piperidin-1-yl)-[1,2,4]thiadiazol-5-yl]-piperazine
- 1-[2-(3,4-Difluoro-phenyl)-ethyl]-4-(3-pyrrolidin-1-yl-[1,2,4]thiadiazol-5-yl)-piperazine
- Cyclopropylmethyl-(5-{4-[2-(3,4-difluoro-phenyl)-ethyl]-piperazin-1-yl}-[1,2,4]thiadiazol-3-yl)-amine
- (5-{4-[2-(3,4-Difluoro-phenyl)-ethyl]-piperazin-1-yl}-[1,2,4]thiadiazol-3-yl)-(tetrahydro-pyran-4-yl)-amine
- Cyclohexyl-(5-{4-[2-(3,4-difluoro-phenyl)-ethyl]-piperazin-1-yl}-[1,2,4]thiadiazol-3-yl)-amine
- 1-[2-(3,4-Difluoro-phenyl)-ethyl]-4-(3-piperidin-1-yl-[1,2,4]thiadiazol-5-yl)-piperazine
- (5-{4-[2-(3,4-Difluoro-phenyl)-ethyl]-piperazin-1-yl}-[1,2,4]thiadiazol-3-yl)-(4-trifluoromethyl-cyclohexyl)-amine
- Butyl-(5-{4-[2-(3,4-difluoro-phenyl)-ethyl]-piperazin-1-yl}-[1,2,4]thiadiazol-3-yl)-ethyl-amine
- 1-(3-Cyclohexyl-[1,2,4]thiadiazol-5-yl)-4-[2-(4-methoxy-phenyl)-ethyl]-piperazine
- 1-(3-Cyclohexyl-[1,2,4]thiadiazol-5-yl)-4-[2-(3-methoxy-phenyl)-ethyl]-piperazine
- 1-(3-Butyl-[1,2,4]thiadiazol-5-yl)-4-[2-(4-methoxy-phenyl)-ethyl]-piperazine
- 1-(3-Cyclopropyl-[1,2,4]thiadiazol-5-yl)-4-[2-(4-methoxy-phenyl)-ethyl]-piperazine
- 1-(3-Butyl-[1,2,4]thiadiazol-5-yl)-4-[2-(3-methoxy-phenyl)-ethyl]-piperazine
- 1-(3-Cyclopropyl-[1,2,4]thiadiazol-5-yl)-4-[2-(3-methoxy-phenyl)-ethyl]-piperazine
- 1-[2-(4-Fluoro-phenyl)-ethyl]-4-[3-(tetrahydro-pyran-4-yl)-[1,2,4]thiadiazol-5-yl]-piperazine
- 1-[2-(4-Methoxy-phenyl)-ethyl]-4-[3-(tetrahydro-pyran-4-yl)-[1,2,4]thiadiazol-5-yl]-piperazine
- 1-[2-(2-Methoxy-pyridin-4-yl)-ethyl]-4-[3-(tetrahydro-pyran-4-yl)-[1,2,4]thiadiazol-5-yl ]-piperazine
- 1-[2-(3,4-Difluoro-phenyl)-ethyl]-4-[3-(tetrahydro-pyran-4-yl)-[1,2,4]thiadiazol-5-yl]-piperazine
- 3-((3-chlorophenoxy)methyl)-5-(4-(3-methoxyphenethyl)piperazin-1-yl)-1,2,4-thiadiazole
- 3-(2-(benzyloxy)ethyl)-5-(4-(3-methoxyphenethyl)piperazin-1-yl)-1,2,4-thiadiazole
- 3-((4-fluorophenoxy)methyl)-5-(4-(3-methoxyphenethyl)piperazin-1-yl)-1,2,4-thiadiazole
- 3-((4-fluorophenoxy)methyl)-5-(4-(4-methoxyphenethyl)piperazin-1-yl)-1,2,4-thiadiazole
- 5-(4-(4-methoxyphenethyl)piperazin-1-yl)-3-(trifluoromethyl)-1,2,4-thiadiazole
- 1-(2-Methyl-benzyl)-4-[3-(tetrahydro-pyran-4-yl)-[1,2,4]thiadiazol-5-yl]-piperazine or
- 3-(4-chlorophenethyl)-5-(4-(2-methylbenzyl)piperazin-1-yl)-1,2,4-thiadiazole.

15. A pharmaceutical composition containing one or more compounds as claimed in claim 14 and pharmaceutically acceptable excipients.

\* \* \* \* \*